(12) United States Patent
Gurumohan et al.

(10) Patent No.: US 10,324,075 B2
(45) Date of Patent: Jun. 18, 2019

(54) TRANSMITTER AND RECEIVER CONFIGURATION FOR DETECTING CONTENT LEVEL

(71) Applicant: Nectar, Inc., Palo Alto, CA (US)

(72) Inventors: Prabhanjan C. Gurumohan, Mountain View, CA (US); Aayush Phumbhra, Palo Alto, CA (US); Samuel Bae, Saratoga, CA (US)

(73) Assignee: Nectar, Inc., Palo Alto, CA (US)

( * ) Notice: Subject to any disclaimer, the term of this patent is extended or adjusted under 35 U.S.C. 154(b) by 0 days.

(21) Appl. No.: 15/454,882

(22) Filed: Mar. 9, 2017

(65) Prior Publication Data

US 2018/0164142 A1 Jun. 14, 2018

Related U.S. Application Data

(63) Continuation-in-part of application No. 14/676,432, filed on Apr. 1, 2015, which is a continuation-in-part of application No. 14/627,719, filed on Feb. 20, 2015, now Pat. No. 10,072,964, application No. 15/454,882, filed on Mar. 9, 2017, which is a continuation-in-part of application No. 14/725,979,
(Continued)

(51) Int. Cl.
*G01F 22/00* (2006.01)
*G01F 23/00* (2006.01)
*G01N 33/14* (2006.01)
*G01F 23/296* (2006.01)

(52) U.S. Cl.
CPC .............. *G01N 33/14* (2013.01); *G01F 22/00* (2013.01); *G01F 23/0076* (2013.01); *G01F 23/2962* (2013.01)

(58) Field of Classification Search
CPC ...... G01N 33/14; F01F 23/296; G01F 23/296; G01F 23/2962; G01F 23/0076; G01F 22/00
See application file for complete search history.

(56) References Cited

U.S. PATENT DOCUMENTS 4,386,409 A 5/1983 Petroff
4,697,200 A 9/1987 Miyatake
(Continued)

OTHER PUBLICATIONS

Amanda Macmillan. It's the Water Bottle of the Future—and You can Pre-Order It Now! Fitness (Flash/Fitness-Blog/) Oct. 7, 2013. http://www.self.com/flash/fitness-blog/2013/10/fitness-water-bottle-of-the-future/.
(Continued)

*Primary Examiner* — Bryan Bui
(74) *Attorney, Agent, or Firm* — Van Pelt, Yi & James LLP

(57) ABSTRACT

A measurement device includes a transmitter configured to transmit an interrogation signal. The measurement device also includes a receiver configured to receive the interrogation signal that has been reflected within a container. The received reflected interrogation signal corresponds to a fill level of the container. A protective barrier covers at least the transmitter or the receiver. If the protective barrier covers the transmitter, the transmitter transmits the interrogation signal through the protective barrier and the transmitter and the protective barrier are separated by a gap.

20 Claims, 16 Drawing Sheets

Related U.S. Application Data filed on May 29, 2015, now Pat. No. 10,078,003, application No. 15/454,882, filed on Mar. 9, 2017, which is a continuation-in-part of application No. 14/627,719, filed on Feb. 20, 2015, now Pat. No. 10,072,964, application No. 15/454,882, filed on Mar. 9, 2017, which is a continuation-in-part of application No. 14/758,000, filed on Dec. 23, 2015, which is a continuation-in-part of application No. 14/725,979, filed on May 29, 2015, now Pat. No. 10,078,003.

(60) Provisional application No. 62/093,890, filed on Dec. 18, 2014, provisional application No. 61/975,337, filed on Apr. 4, 2014, provisional application No. 62/006,419, filed on Jun. 2, 2014, provisional application No. 62/007,841, filed on Jun. 4, 2014, provisional application No. 62/093,890, filed on Dec. 18, 2014, provisional application No. 62/007,841, filed on Jun. 4, 2014.

(56) References Cited

U.S. PATENT DOCUMENTS

| | | | |
|---|---|---|---|
| 4,698,541 A | 10/1987 | Bar-Cohen | |
| 4,782,451 A | 11/1988 | Mazzarella | |
| 4,823,600 A | 4/1989 | Biegel | |
| 4,934,191 A | 6/1990 | Kroening | |
| 4,961,456 A | 10/1990 | Stembridge | |
| 5,042,698 A | 8/1991 | Fessell | |
| 5,150,334 A | 9/1992 | Crosby | |
| 5,303,585 A | 4/1994 | Lichte | |
| 5,389,848 A | 2/1995 | Trzaskos | |
| 5,471,872 A | 12/1995 | Cummings | |
| 5,603,430 A | 2/1997 | Loehrke | |
| 5,866,815 A | 2/1999 | Schwald | |
| 5,880,364 A | 3/1999 | Dam | |
| 6,272,921 B1 | 8/2001 | Ivanovich | |
| 6,545,946 B1 | 4/2003 | Huss | |
| 6,856,247 B1 | 2/2005 | Wallace | |
| 7,068,805 B2 | 6/2006 | Geddes | |
| 7,088,258 B2 | 8/2006 | Morrison | |
| 7,109,863 B2 | 9/2006 | Morrison | |
| 7,190,278 B2 | 3/2007 | Morrison | |
| 7,495,558 B2 | 2/2009 | Pope | |
| 7,573,395 B2 | 8/2009 | Morrison | |
| 7,598,883 B2 | 10/2009 | Morrison | |
| 8,061,198 B2 | 11/2011 | Yinko | |
| 8,151,596 B2 | 4/2012 | Richmond | |
| 8,284,068 B2 | 10/2012 | Johnson | |
| 8,851,740 B1 | 10/2014 | Mills | |
| 9,506,798 B2 | 11/2016 | Saltzgiver | |
| 9,508,484 B2 | 11/2016 | Scholz | |
| 2002/0059828 A1 | 5/2002 | Muller | |
| 2004/0169600 A1 | 9/2004 | Haynes | |
| 2005/0033532 A1 | 2/2005 | Mogadam | |
| 2005/0072226 A1 | 4/2005 | Pappas | |
| 2005/0268715 A1 | 12/2005 | Sabatino | |
| 2006/0201245 A1 | 9/2006 | Huber | |
| 2006/0231109 A1 | 10/2006 | Howell | |
| 2006/0270421 A1 | 11/2006 | Phillips | |
| 2007/0008212 A1 | 1/2007 | Serban | |
| 2007/0125162 A1 | 6/2007 | Ghazi | |
| 2007/0261487 A1 | 11/2007 | Sintes | |
| 2008/0154522 A1 | 6/2008 | Welle | |
| 2008/0250869 A1* | 10/2008 | Breed | B60C 11/24 73/861.27 |
| 2008/0297403 A1 | 12/2008 | Akerstrom et al. | |
| 2008/0314807 A1 | 12/2008 | Junghanns | |
| 2009/0093983 A1 | 4/2009 | Trafford | |
| 2009/0134183 A1 | 5/2009 | Odishoo | |
| 2010/0070208 A1 | 3/2010 | Sai | |
| 2010/0101317 A1 | 4/2010 | Ashrafzadeh | |
| 2010/0108635 A1 | 5/2010 | Horstman | |
| 2010/0200593 A1 | 8/2010 | Lazar | |
| 2010/0270257 A1 | 10/2010 | Wachman | |
| 2011/0042408 A1 | 2/2011 | Giordano | |
| 2011/0166699 A1 | 7/2011 | Palmquist | |
| 2011/0169635 A1 | 7/2011 | Johnson | |
| 2012/0052802 A1 | 3/2012 | Kasslin | |
| 2012/0206155 A1 | 8/2012 | Wang | |
| 2013/0073218 A1 | 3/2013 | Haas | |
| 2013/0122817 A1 | 5/2013 | Pivaudran | |
| 2013/0222135 A1 | 8/2013 | Stein | |
| 2013/0313204 A1 | 11/2013 | Shalon | |
| 2014/0149265 A1 | 5/2014 | Kundra | |
| 2014/0208845 A1 | 7/2014 | Zlotnick | |
| 2014/0324585 A1 | 10/2014 | Mederos | |
| 2014/0360270 A1 | 12/2014 | Koenig | |
| 2015/0101405 A1 | 4/2015 | Gorenflo | |
| 2015/0334079 A1 | 11/2015 | Laidlaw | |
| 2015/0355012 A1 | 12/2015 | Gurumohan | |
| 2016/0025545 A1 | 1/2016 | Saltzgiver | |
| 2016/0146659 A1 | 5/2016 | Saltzgiver | |
| 2016/0178426 A1 | 6/2016 | Gurumohan | |
| 2016/0194190 A1 | 7/2016 | Fogg | |
| 2016/0198246 A1 | 7/2016 | Gurumohan | |

OTHER PUBLICATIONS

Jonah Comstock. Slideshow: 8 Pillboxes that Connect to Your Phone. Mobihealth News. Mar. 13, 2013. http://mobihealthnews.com/20795/slideshow-8-pillboxes-that-connect-to-your-phone/2/.

\* cited by examiner

TRANSMITTER AND RECEIVER CONFIGURATION FOR DETECTING CONTENT LEVEL

CROSS REFERENCE TO OTHER APPLICATIONS

This application is a continuation-in-part of co-pending U.S. patent application Ser. No. 14/676,432 entitled CONTAINER CONTENT QUANTITY MEASUREMENT AND ANALYSIS filed Apr. 1, 2015, which is a continuation-in-part of co-pending U.S. patent application Ser. No. 14/627,719 entitled CONTAINER FILL LEVEL MEASUREMENT AND MANAGEMENT filed Feb. 20, 2015, which claims priority to U.S. Provisional Patent Application No. 62/093,890 entitled CONTAINER FILL LEVEL MEASUREMENT AND MANAGEMENT filed Dec. 18, 2014. U.S. patent application Ser. No. 14/676,432 claims priority to U.S. Provisional Patent Application No. 61/975,337 entitled SYSTEMS AND METHODS FOR CONSUMER FOOD AND NUTRITION MANAGEMENT filed Apr. 4, 2014, and claims priority to U.S. Provisional Patent Application No. 62/006,419 entitled SYSTEM AND METHODS FOR FOOD AND BEVERAGE TRACKING, REPLENISHMENT AND CONSUMPTION MANAGEMENT filed Jun. 2, 2014, all of which are incorporated herein by reference for all purposes.

This application is a continuation-in-part of co-pending U.S. patent application Ser. No. 14/725,979 entitled SENSOR DEVICE CONFIGURATION filed May 29, 2015, which claims priority to U.S. Provisional Patent Application No. 62/007,841 entitled BEVERAGE TRACKING, REPLENISHMENT, CONSUMPTION AND INVENTORY MANAGEMENT filed Jun. 4, 2014, both of which are incorporated herein by reference for all purposes.

This application is a continuation-in-part of co-pending U.S. patent application Ser. No. 14/627,719 entitled CONTAINER FILL LEVEL MEASUREMENT AND MANAGEMENT filed Feb. 20, 2015, which claims priority to U.S. Provisional Patent Application No. 62/093,890 entitled CONTAINER FILL LEVEL MEASUREMENT AND MANAGEMENT filed Dec. 18, 2014, both of which are incorporated herein by reference for all purposes.

This application is a continuation-in-part of co-pending U.S. patent application Ser. No. 14/758,000 entitled INTERROGATION SIGNAL PARAMETER CONFIGURATION filed Dec. 23, 2015, which is a continuation-in-part of co-pending U.S. patent application Ser. No. 14/725,979 entitled SENSOR DEVICE CONFIGURATION filed May 29, 2015, which claims priority to U.S. Provisional Patent Application No. 62/007,841 entitled BEVERAGE TRACKING, REPLENISHMENT, CONSUMPTION AND INVENTORY MANAGEMENT filed Jun. 4, 2014, all of which are incorporated herein by reference for all purposes.

BACKGROUND OF THE INVENTION

Certain items such as food and beverages are often sold and stored in product containers. In many instances, a consumer periodically performs a visual check to inventory contents remaining in food and beverage containers. In another example, bar and restaurant operators periodically inventory the amount of content left in bottles to determine the amount sold and identify quantity and type of products to be purchased/replenished. The inventory of content remaining in product containers has been traditionally determined manually. This manual process is often laborious, imprecise, and error prone. For example, it is often difficult for a person to visually determine an amount of liquid beverage remaining in a bottle with precision in a reliable manner. In commercial settings, the amount of time spent by an employee to manually inventory the remaining content represents a real employment cost realized by the employer. Therefore, there exists a need for a better way to determine the amount of content remaining in a container.

BRIEF DESCRIPTION OF THE DRAWINGS

Various embodiments of the invention are disclosed in the following detailed description and the accompanying drawings.

DETAILED DESCRIPTION

Figure 1:
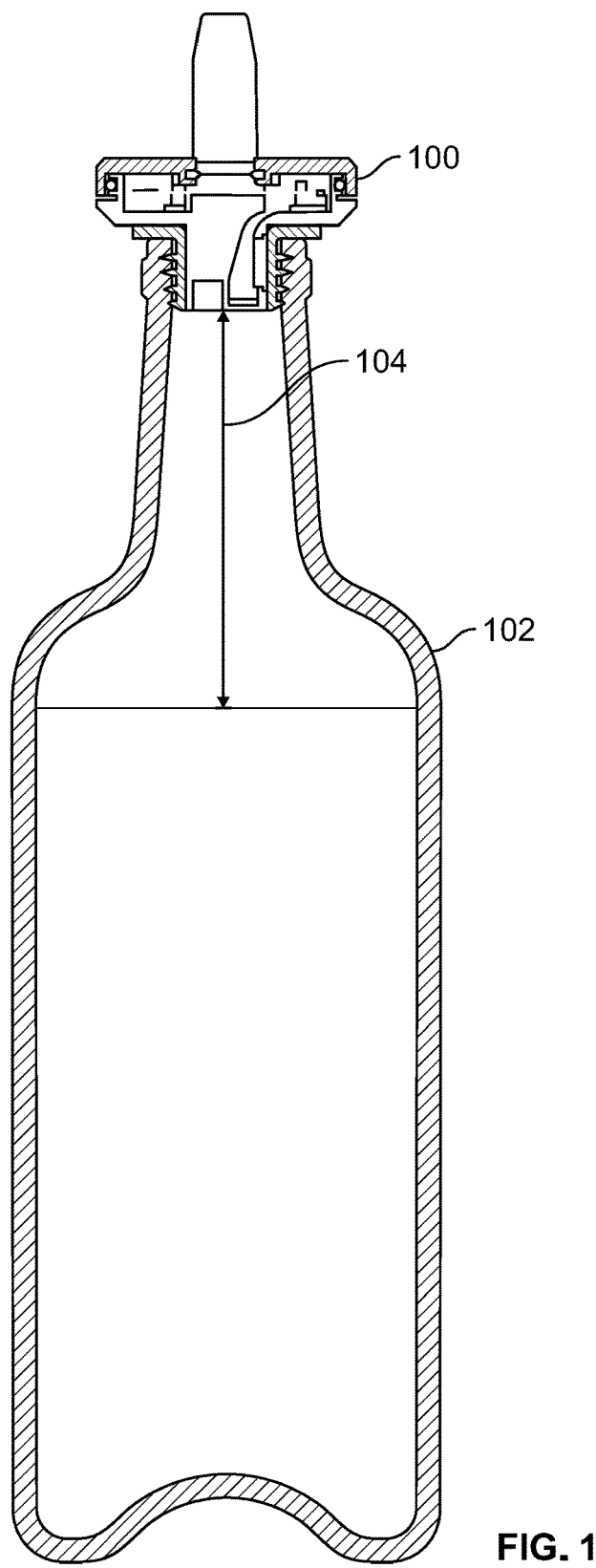
FIG. 1 is a diagram illustrating an embodiment of a fill level sensor device engaged in a container.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A sensor device is disclosed. For example, the sensor device is a container cover (e.g., sensor device also functions as a bottle cap) that electronically measures an amount of liquid remaining in a container (e.g., beverage bottle) covered by the container cover. In some embodiments, the sensor device includes a content level sensor. For example, the sensor transmits an ultrasonic signal and measures the amount of time it takes for the signal to bounce off a liquid content remaining in the container and return back to the sensor to determine the liquid level remaining in the container. The sensor device includes a transmitter that transmits an interrogation signal. For example, a speaker transmits an ultrasonic signal. The sensor device also includes a receiver that receives the interrogation signal that has been reflected within a container. For example, the received interrogation signal is processed to determine a fill level of the container.

In some embodiments, the transmitter and receiver are configured to be located within an interior of the container when the container cover engages the container. Because the transmitter and receiver may be adversely damaged/affected by contents of the container while inside the container, the transmitter and receiver may be required to be protected from the contents of the container. For example, alcohol or acidic beverages may damage the receiver/transmitter if it comes in direct contact. In some embodiments, a protective material (e.g., barrier film) covers at least the transmitter and/or the receiver. The protective material may protect the transmitter from direct exposure to contents of the container. However, the protective material may adversely affect the quality of the transmitted signal required to accurately detect the fill level of the container. In order to be able to effectively transmit the interrogation signal through the protective material, the transmitter and the protective material are positioned to create an engineered gap of a preset distance to allow the protective material to effectively transmit the interrogation signal. For example, effective vibration of the protective material may be achieved at a certain distance between the transmitter and the protective material without directly attaching the transmitter to the protective material. In some embodiments, the protective material (e.g., barrier film) covers the receiver and the receiver receives through the protective material the transmitted signal that has been reflected by contents of the container.

In some embodiments, the sensor device includes a sensor that detects that the device has been triggered. For example, an accelerometer/motion sensor included in the sensor device detects that the device has been moved. This movement may correspond to consuming contents from the container that is engaged with the sensor device (e.g., bottle cap with sensor removed from bottle to pour contents out of the bottle, bottle tipped over to pour contents out of a spout on the sensor device that also functions as a pourer, etc.) and the trigger initiates a measurement of a fill level of contents in the container. Because it is power intensive to perform the measurement, using the triggering condition to initiate the measurement allows power to be conserved from not having to perform measurements when the triggering condition is not met.

When the transmitter of the sensor device transmits an ultrasonic signal, the amount of time it takes for the signal to bounce off content remaining in the container and return back to the sensor is measured to determine the amount of content remaining in the container. However, not only does the reflected signal reflect off the content remaining in the container in a direct path, the transmitted signal reflects off walls of the container as well as the contents of the container in non-direct paths. Because multiple reflections are received by a receiver of the sensor device, the actual direct reflection that indicates the current fill level of the container needs to be identified among various detected reflections. For example, each reflection corresponds to different distances traveled by the interrogation signal and consequently corresponds to different potential container fill levels. One of the reflections is selected as the selected reflection that corresponds to a selected container fill level. For example, the reflection that corresponds to a smallest change from a previously determined fill level is selected as the selected reflection. This may allow the selected reflection to correspond to the shortest distance/direct reflection path from the transmitter to the contents of the container. This selected container fill level is utilized to provide the current detected container fill level.

FIG. 1 is a diagram illustrating an embodiment of a fill level sensor device engaged in a container. Container 102 is filled with a liquid. In the example shown, fill level sensor device 100 is configured as a container cover (e.g., a bottle cap pourer with a spout). The liquid fill level of container 102 may be determined by measuring the distance between sensor device 100 and the liquid surface of container 102. As shown by line 104, a transmitter of sensor device 100 sends out a signal (e.g., ultrasonic signal) that gets reflected by the surface of the liquid. The reflected signal is detected by a receiver of sensor device 100.

By measuring the amount of time it took to receive the reflected signal, the distance traveled by the signal before being reflected (e.g., distance between sensor device 100 and liquid surface is half of the total distance traveled by the signal) may be determined by multiplying the amount of time by the speed of the signal (e.g., speed of sound).

In some embodiments, to determine the amount of time it took to receive the reflected signal, the received reflected signal is filtered to isolate the desired signal (e.g., band-pass filter the received signal), amplified, and analyzed to detect peaks that correspond to when the reflected signal was received. A predetermined beginning portion (e.g., predetermined amount of time in the beginning of the signal) of the received signal may be ignored when analyzing the signal to ignore signals that were detected due to coupling between the transmitter and receiver of sensor device 100. For example, when the transmitter transmits the signal, the signal may be received by the receiver of sensor device 100 (e.g., conducted through sensor device 100, due to undesired reflection, etc.) before the signal is reflected by the contents of the container, and the undesired received signals received in the beginning portion of the received signal are ignored when identifying the desired received reflected signal.

If the total distance between the bottom of container 102 and sensor device 100 is known, the fill height of container 102 can be determined (e.g., total distance between bottom and sensor device 100 minus distance between sensor device 100 and liquid surface). If the shape and volume of the bottle are known, the volume of liquid contained in container 102 may be determined. For example, a table/database/data structure that maps fill level (e.g., fill height, height between liquid surface and sensor device 100, etc.) to liquid volume of the container is utilized to determine liquid volume corresponding to the determined fill level. Different tables/databases/data structures may exist for different types of containers.

Figure 2A:
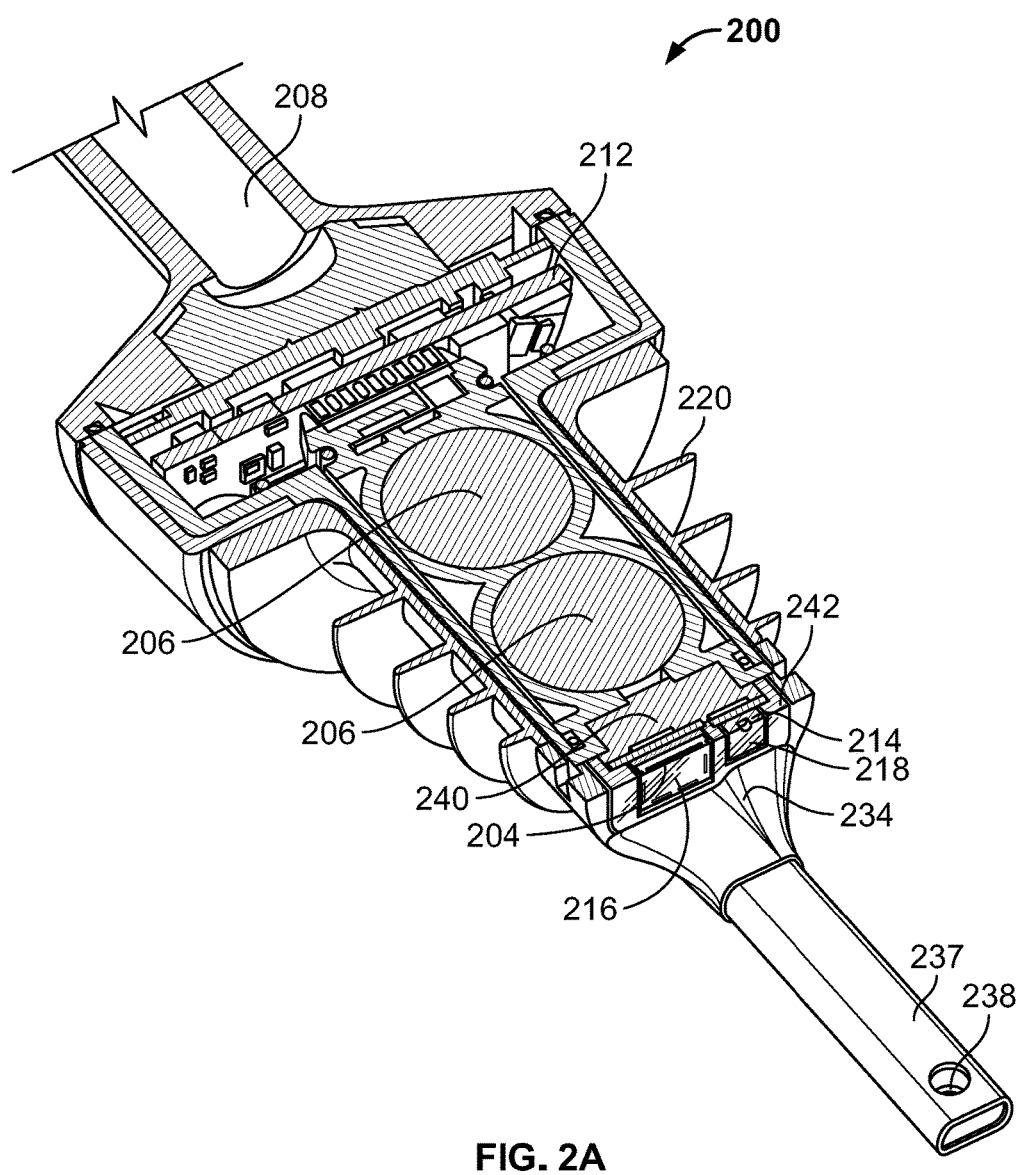
FIG. 2A is an example profile cross-sectional diagram illustrating an embodiment of a fill level sensor device.
Figure 2B:
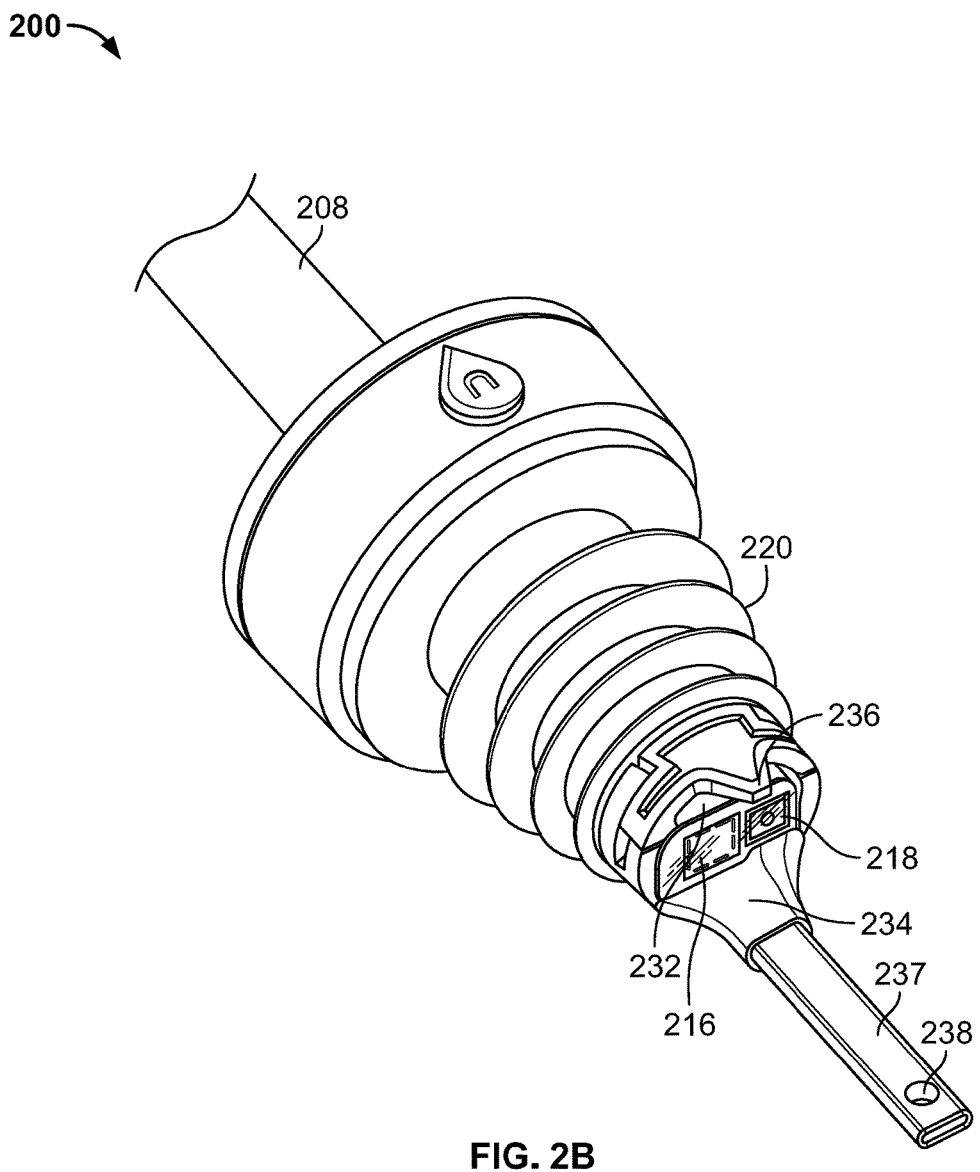
FIG. 2B is an example side cross-sectional diagram illustrating the sensor device of FIG. 2A.
Figure 2C:
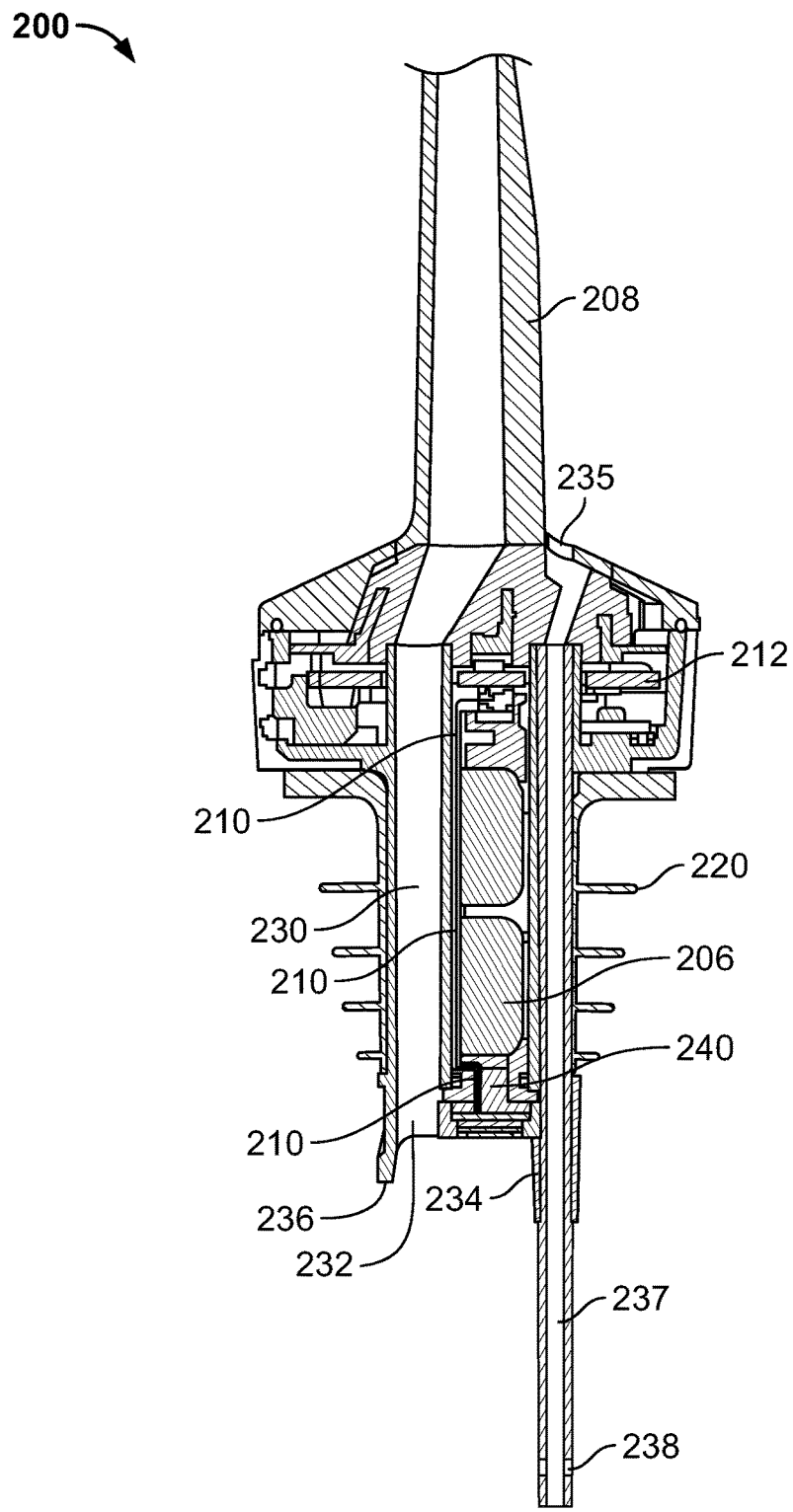
FIG. 2C is an example diagram of an external profile view of the sensor device of FIG. 2A.
Figure 2D:
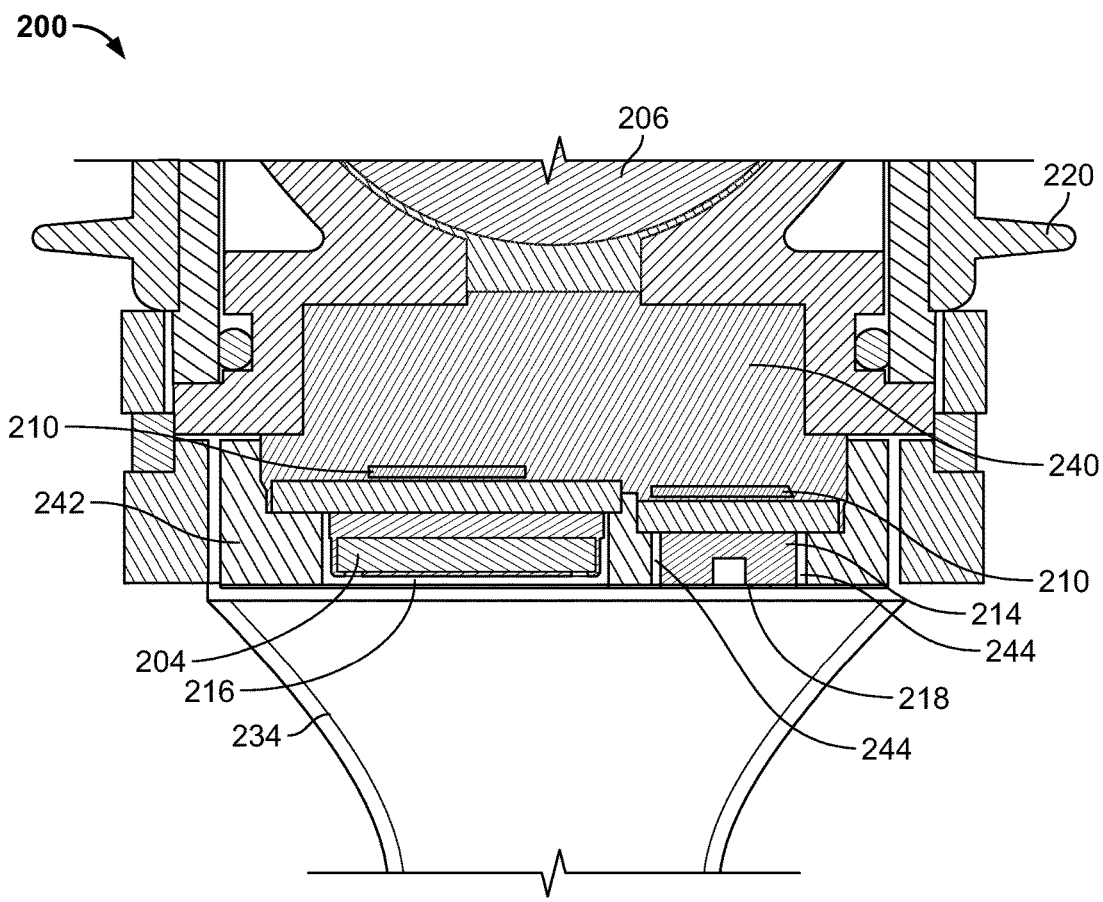
FIG. 2D is an example diagram of a bottom region close up view of the sensor device of FIG. 2A.

FIG. 2A is an example profile cross-sectional diagram illustrating an embodiment of a fill level sensor device. FIG. 2B is an example side cross-sectional diagram illustrating the sensor device of FIG. 2A. FIG. 2C is a diagram illustrating an example external profile view of the sensor device of FIG. 2A. FIG. 2D is a diagram illustrating an example bottom region close up view of the sensor device of FIG. 2A. In some embodiments, sensor device 200 is sensor device 100 of FIG. 1. In the examples shown, sensor device 200 is configured to function as a bottle stopper with a spout. Sensor device 200 includes flexible container coupling ridges 220 (e.g., elastomer/rubber rings) that allow sensor device 200 to be coupled to and seal an opening of a container. However, in other embodiments, sensor device 200 may be configured as a different cover of a container. For example, the components of sensor device 200 may be included in a screw-on cap or any other cap that engages a container.

Sensor device 200 includes circuit board 212. For example circuit board 212 is a printed circuit board. Circuit board 212 may connect together one or more of the following included in sensor device 200: a processor, a memory, a data storage, a connector, an integrated chip, a transmitter, a receiver, an accelerometer, a tilt sensor, an orientation sensor, a solar panel, a display, a gyroscope, a wireless data communication signal transmitter (e.g., a component able to communicate using Bluetooth, Wi-Fi, other wireless protocol, etc.), and other electrical components. For example, a processor connected to circuit board 212 provides a command to transmit an acoustic signal using a transmitter and processes a received signal to determine a fill level indicator. The fill level indicator may be transmitted wirelessly to another device such as a mobile device, a computer, a display device, or any other computing or display device using a wireless data communication transmitter. Circuit board 212 is connected to batteries 206. Battery 206 provides power to the circuit of circuit board 212. Battery 206 may be rechargeable and/or replaceable. In the embodiment shown, at least a portion of the batteries are in the neck of sensor device 200. For example, when sensor device 200 is engaged with a container, at least a portion of the batteries are positioned inside the container. By placing the batteries inside the neck of sensor device 200 that is configured to be placed inside the container, space within the neck of sensor device 200 that is otherwise required for ridges 220 to engage with the container is efficiently utilized. As shown in the example, a plurality of batteries may be used and positioned next to each other lengthwise in the neck of sensor device 200. The housing of sensor device 200 may be composed of one or more materials. Examples of the materials include a food grade polymer, elastomer, plastic, rubber (e.g., synthetic or otherwise), stainless steel, and other metals.

Sensor device 200 includes spout 208. Spout 208 is a part of a passage channel (e.g., hollow tube) that allows container contents (e.g., liquid) to pass through to the tip opening of spout 208 from a bottom of sensor device 200. This passage channel is shown as channel 230 and channel 232 in the figures. For example, a liquid contained in a container that is capped by sensor device 200 is able to pass through sensor device 200 and exit the opening of spout 208 when the container capped by sensor device 200 is tipped over. In some embodiments, circuit board 212 includes an opening hole that accommodates the passage channel that allows container contents (e.g., liquid) to pass through the circuit board. In other embodiments, spout 208 may not exist in sensor device 200. In some embodiments, sensor device 200 includes a vent tube that allows air to enter a container capped by sensor device 200 as content of the container is poured out through spout 208. In some embodiments, sensor device 200 includes a motor (not shown) that pumps out contents of the container capped by sensor device 200. Air vent 235 allows air to enter the container when container contents are poured out of spout 208. Air vent 235 allows air to flow to the bottom of sensor device 200 (e.g., into container) via the channel of vent tube 237. The length of vent tube has been specifically selected to achieve a desired flow rate out of spout 208. In various embodiments, the length of vent tube 237 is between 3-12 centimeters. For example, vent tube 237 is substantially 7 centimeters in length. Vent tube 237 is sealed/blocked at the end of the vent tube. Instead of allowing air to flow via this blocked end, vent tube 237 includes side holes 238 where air from air vent 235 may pass. By forcing air through side holes 238, the rate of air flow from air vent 235 may be controlled (e.g., rate of flow reduced as compared to having a simple hollow tube with an open end as vent tube). For example, the contents remaining inside channel 230 from pouring contents out of spout 208 may be forced out of spout 208 from pressure differential created from turning the container upright and the controlled air flow may reduce this from happening. In some embodiments, by sealing/blocking the end of vent tube 237, a likelihood that contents of a container would be forced into vent tube 237 when the container is tipped is reduced.

Circuit board 212 is electrically connected to transmitter 204. In some embodiments, transmitter 204 is an acoustic transmitter (e.g., ultrasonic signal transmitter). For example, transmitter 204 is a speaker. In some embodiments, transmitter 204 is a piezoelectric speaker. In some embodiments, transmitter 204 is configured to transmit a signal within the ultrasonic frequencies. In some embodiments, transmitter 204 is configured to transmit a signal between 1 kHz and 400 kHz, inclusive. In some embodiments, transmitter 204 is configured to transmit a 29 kHz to 40 kHz signal. In some embodiments, transmitter 204 is an acoustic impulse generator. Receiver 214 is electrically connected to circuit board 212. In some embodiments, receiver 214 is an acoustic receiver (e.g., ultrasonic signal receiver). In some embodiments, receiver 214 is a microphone. In some embodiments, receiver 214 is a Micro Electro Mechanical Systems (MEMS) microphone. For example, receiver 214 is 2 millimeter×3 millimeter in size. Receiver 214 and transmitter 204 are connected to circuit board 212 via connector 210. As shown in FIG. 2C, connector 210 is routed from bottom of device 200 via the neck of device 200 to circuit board 212. Examples of connector 210 include a wire, a bus, a flexible printed circuit board, and any other connector able to transmit a signal. For example, connector 210 connects to rear of receiver 214 and transmitter 204 via one or more connectors mounted on receiver 214 and transmitter 204.

In some embodiments, because debris, liquid, and other materials may affect the performance and durability of transmitter 204 and receiver 214 (e.g., when using spout 208 to pour out contents of the container), transmitter 204 and receiver 214 are placed in protected compartments. In some embodiments, a protective layer material covers transmitter 204 and receiver 214. Ideally the protective material must not allow undesired material through while at the same time allowing signals (e.g., acoustic signals) to pass through. Protective material 216 covers transmitter 204 and is attached to edges surrounding the assembly forming the compartment that houses transmitter 204. Protective material 216 covers receiver 214 and is attached to edges surrounding the assembly forming the compartment that houses receiver 214. In some embodiments, protective material 216 and protective material 218 are the same continuous material. For example, a single connected sheet includes both protective material 216 and protective material 218. In some embodiments, protective material 216 and protective material 218 are not continuous materials. For example, in order to maximize decoupling of the transmitted signal of transmitter 204 and the received signal of receiver 214, protective material 216 and protective material 218 are not made of the same continuous material. In some embodiments, protective material 216 and protective material 218 are different materials. Examples of protective material 216 and protective material 218 include one or more of the following: Mylar sheet, waterproof mesh, acoustic sheet, Teflon, Gortek, polytetrafluoroethylene (PTFE), polyethylene terephthalate (PET), polyethylene terephthalate glycol-modified (PETG), polycarbonate, and any other appropriate mesh or membrane that may be porous or non-porous. For example, a Mylar sheet covering does not allow liquid to pass through while acting like a drum to allow acoustic signals to pass through. In some embodiments, protective material 216 and/or protective material 218 are acoustically transmissive liquid blocking materials. In some embodiments, protective material 216 and/or protective material 218 is optional. In some embodiments, protective material 216 and 218 are attached to device 200 via a food-safe adhesive.

A gap distance has been engineered to be between transmitter 204 and protective material 216. For example, transmitter 204 is mounted in a manner that ensures a predetermined gap between transmitter 204 and protective material 216. In various embodiments the gap between transmitter 204 and protective material 216 is approximately 0.2 millimeters. For example, in order to be able to effectively transmit the interrogation signal through the protective material, the transmitter and the protective material are positioned to create an engineered gap of a preset distance to allow protective material to effectively transmit the interrogation signal. Effective vibration of the protective material may be achieved at a certain distance (e.g., resonance distance) between the transmitter and the protective material without directly attaching the transmitter to the protective material. In some embodiments, the gap is an air gap between transmitter 204 and protective material 216. In various embodiments the gap may include other gases, liquids and/or solids placed between transmitter 204 and protective material 216 to achieve desired signal transmission properties via the gap and the protective material.

In some embodiments, receiver 214 is in direct contact with protective material 218. For example, receiver 214 is mounted in a manner that ensures that receiver 214 contacts protective material 218. For example, in order to be able to effectively receive the reflected interrogation signal through the protective material, the receiver is in contact with the protective material. In some embodiments, receiver 214 is attached to protective material 218 via adhesive (e.g., pressure sensitive adhesive). For example, a surface of receiver 214 is coated with the adhesive and allowed to be attached to protective material 218.

Transmitter 204 and receiver 214 are sealed and attached to assembly 242 of device 200 using a potting material. For example, a cavity behind transmitter 204 and receiver 214 within an assembly of device 200 is filled with the potting material to secure the transmitter and the receiver from movement as well as minimize/isolate direct signal transmission (e.g., minimize signal directly reaching from transmitter to receiver via the housing of device 200). As shown in the figures, potting material 240 fills the cavity behind transmitter 204 and receiver 214. For example, the potting material has been injected into the cavity via an opening in the assembly of device 200. Potting material 240 may be a solid or gelatinous compound. For example, plastics, silicone, epoxy, elastomer, and/or rubber (e.g., synthetic or otherwise) may be utilized as potting material 240.

In some embodiments, in order to dampen the signal/vibration/noise reaching receiver 214 (e.g., conducted at least through assembly 242 from transmitter 204), at least a portion of receiver 214 is placed in contact with (e.g., coupled to) a dampening material. For example, at least a portion of one or more sides and/or front of receiver 214 contacts the dampening material (e.g., placed between assembly 242 and receiver 214). Examples of the dampening material include foam, elastomer, rubber (e.g., synthetic or otherwise), silicone and/or polymer. In some embodiments, the dampening material is included in at least a portion of region 244 between assembly 242 and receiver 214 (e.g., receiver 214 is seated in the dampening material that is placed within assembly 242 and the dampening material contacts both receiver 214 and assembly 242).

Device 200 includes drip collectors 234 and 236. Because the bottom of device 200 is exposed to the content of the container when device 200 is engaged with the container, liquid or other content of the container may bead on and attach to device 200 (e.g., when the sensor is tipped over to pour out contents via the spout or when the contents splash in the container during movement and transport). Beading of contents on device 200 may interfere with signal transmission and detection required to detect fill levels of the container. For example, when liquid beads form on protective material 216 and/or protective material 218, it may interfere with signal transmission of transmitter 204 and/or signal receipt of receiver 214. In order to reduce the chances of content remaining on the surfaces of protective material 216 and/or protective material 218, drip collectors 234 and 236 have to be shaped to pull away content remaining on the bottom of device 200. For example, when device 200 is placed upright, the slope of the drip collectors aids the gravitational pull of any beaded content away from the drip collectors to back down into the container. When beaded content on the drip collector is pulled down along the slope of the drip collectors by gravitational forces, beaded content remaining on protective materials 216 and 218 may also be pulled along the slope of the drip collectors back down into the container. In some embodiments, drip collectors 234 and 236 aids in the breaking of the surface tension of content deposited on protective materials 216 and/or 218 by wicking away the content with the aid of the slope of the drip collectors 234 and 236 that leverages the gravitational pull down the slope the drip collectors.

As shown in the figures, drip collector 234 is adjacent to protective materials 216 and 218 and forms a slope connecting a horizontal surface of protective materials 216 and 218 to a perpendicular vertical surface. Drip collector 234 is adjacent to the opening of channel 232 and aids in the removal of content beading/forming on the lip of channel 232 and protective materials 216 and 218. The tip (e.g., narrowing surface) formed by the shape of drip collectors 234 and 236 allows concentration of content as the content flows down the drip collectors to allow concentration of content that aids to increase gravitational pull and reduce surface tension. In some embodiments, channel 232 does not exist (e.g., bottle stopper sensor device) and drip collector 236 is shaped to form a slope from the plane of protective materials 216 and 218 to the vertical tip of drip collector 236. The surface of drip collectors 234 and 236 have been formed and/or coated to be substantially smooth (e.g., to further reduce friction/tension).

In an alternative embodiment, rather than utilizing a separate transmitter and a separate receiver, a transceiver that acts as both a receiver and transmitter is utilized. For example, receiver 214 is not utilized and transmitter 204 is a transceiver (e.g., piezoelectric transceiver).

Figure 3A:
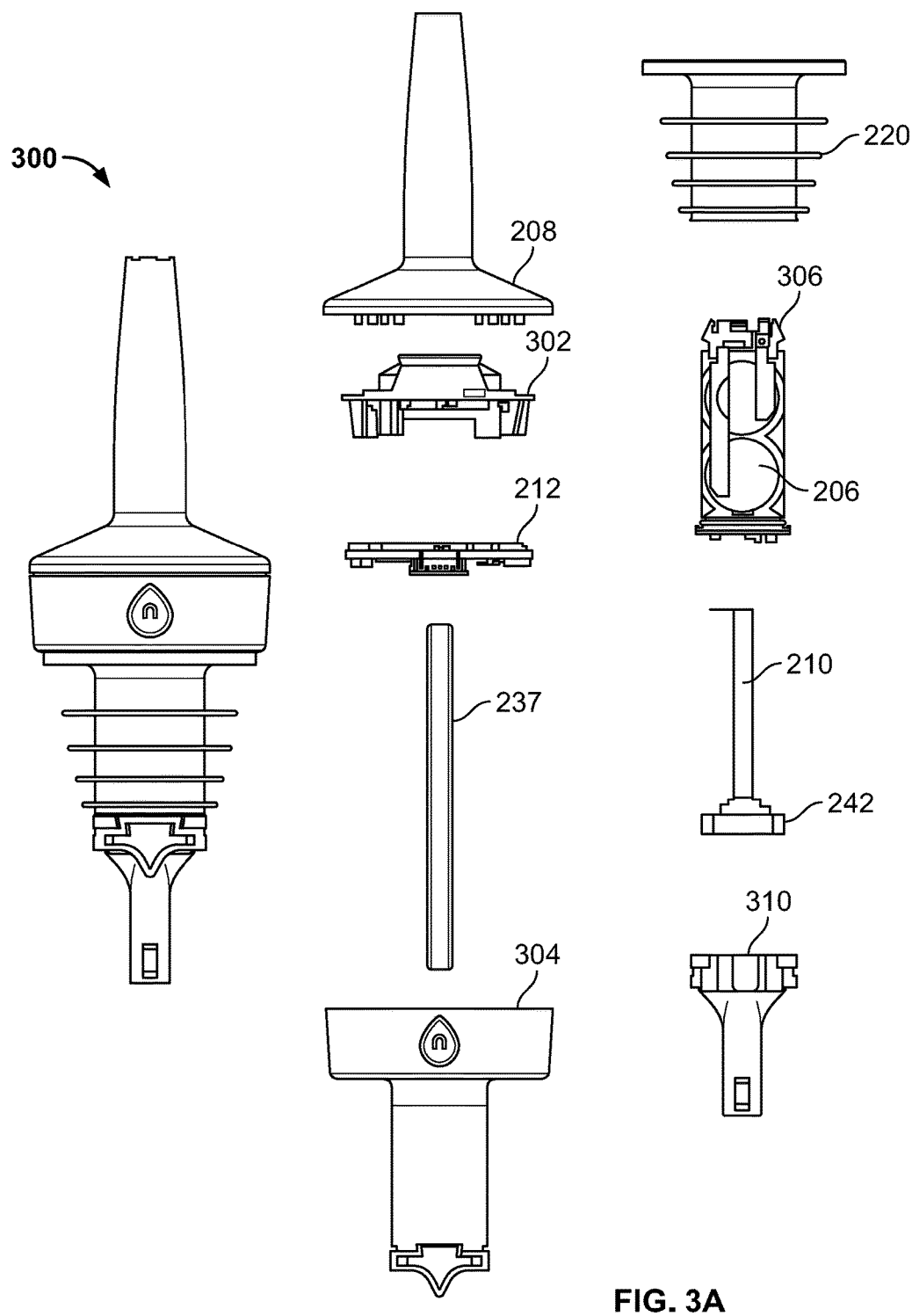
FIG. 3A is a diagram showing components of a pourer fill level sensor.

FIG. 3A is a diagram showing components of a pourer fill level sensor. FIG. 3A shows components of fill level sensor device 300. Fill level sensor device 300 is an example of a fill level sensor device 200 with a pouring spout shown in FIGS. 2A-2D.

Pour spout 208 is made of metal and coated with metal (e.g., chrome). This may aid in the durability and pour flow rate. Sealing spacer 302 seals the content pour channel as the air vent channel between components and also functions as a spacer for assisting the alignment of circuit board 212 during assembly. Circuit board 212 includes one or more holes to accommodate the pour channel and the air vent channel. Vent tube 237 includes metal components and extends from a vent hole on pour spout 208 through sealing spacer 302 and circuit board 212 and through drip collector 310 that includes drip collector 234.

Housing 304 includes plastic and elastomer components. Elastomer rings 220 fit over the neck portion of housing 304. Battery holder 306 includes batteries 206 and is inserted inside the neck of housing 304. Battery holder 306 allows connector 210 to be routed from one end of the battery holder 306 near the transmitter and receiver to the other end of battery holder 306 to allow connector 210 to connect the transmitter and receiver to circuit board 212. Sensor holder assembly 242 includes a frame to position a transmitter and a receiver in assembly 242. Holder assembly 242 includes a raised edged surface where a protective material (e.g., materials 216 and 218) is attached to cover the transmitter and receiver. Holder assembly 242 is configured to be coupled to an end of battery holder 306 such that backsides of the transmitter and receiver face battery holder 306. After battery holder 306 and holder assembly 242 are coupled together, a potting material may be injected into a cavity between them to attach battery holder 306 and holder assembly 242 together as well as seal the transmitter and receiver within the holder assembly 242 (e.g., backsides of the transmitter and receiver are exposed and attached to the potting material).

In some embodiments, a sealing material seals edges of protective material attached to holder assembly 242 and the external exposed surface of the potting material (e.g., potting material exposed from a hole used to inject the potting material between battery holder 306 and holder assembly 242) to protect them from being damaged by contents (e.g., alcohol, acidic beverage, etc.) of a container.

Figure 3B:
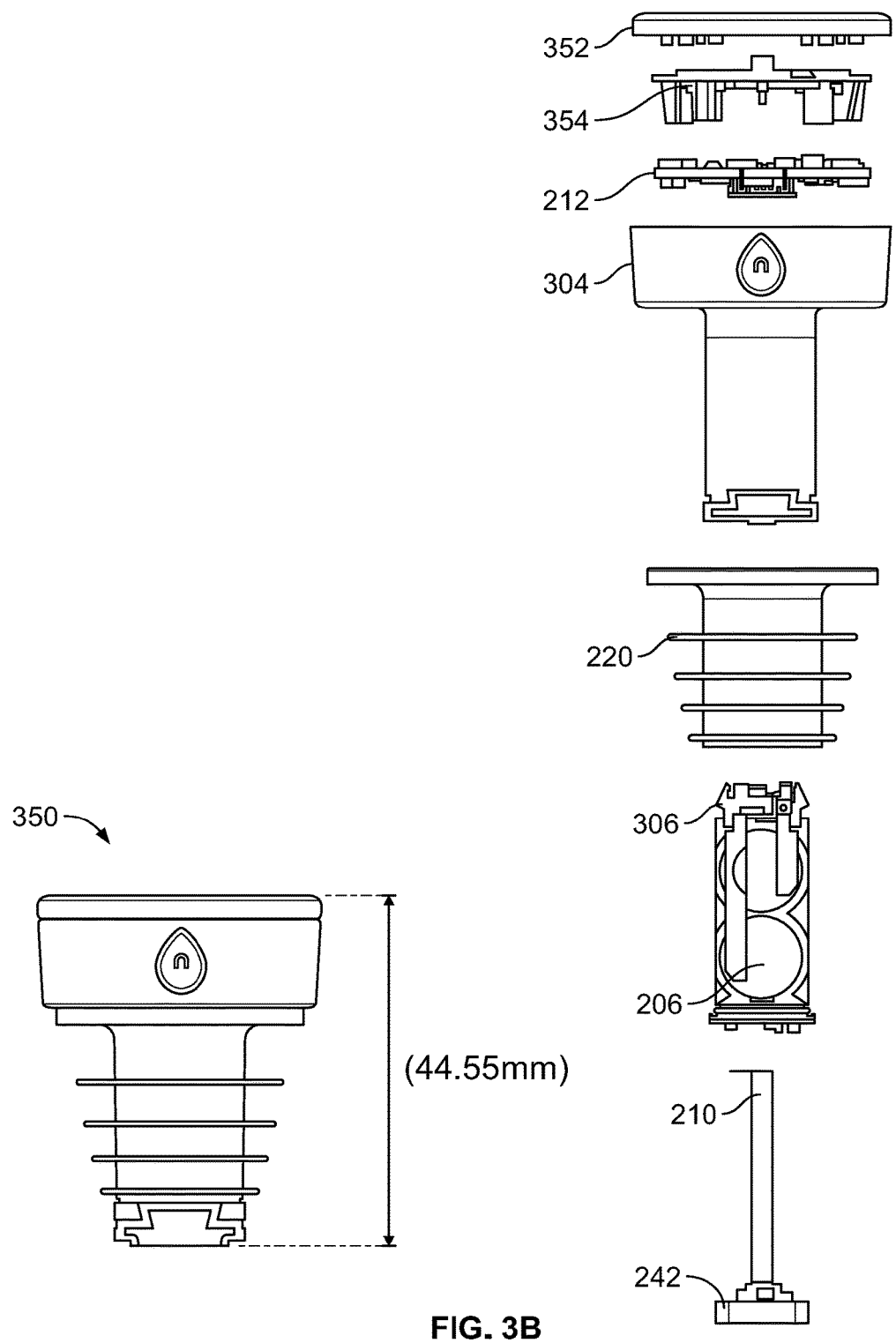
FIG. 3B is a diagram showing components of a stopper fill level sensor.

FIG. 3B is a diagram showing components of a stopper fill level sensor. FIG. 3B shows components of fill level sensor device 350. Fill level sensor device 350 is an example of fill level sensor device 200 without a pouring spout and utilizes many of the same components of fill level sensor 200 shown in FIGS. 2A-2D.

Top cap 352 is made of metal. Spacer 354 assists in the alignment of circuit board 212 during assembly. Housing 304 includes plastic and elastomer components. Elastomer rings 220 fit over the neck portion of housing 304. Battery holder 306 includes batteries 206 and is inserted inside the neck of housing 304. Battery holder 306 allows connector 210 to be routed from one end of the battery holder 306 near the transmitter and receiver to the other end of battery holder 306 to allow connector 210 to connect the transmitter and receiver to circuit board 212. Sensor holder assembly 242 includes a frame to position a transmitter and a receiver in assembly 242. Holder assembly 242 includes a raised edged surface where a protective material layer (e.g., materials 216 and 218) is attached to cover the transmitter and receiver. Holder assembly 242 is configured to be coupled to an end of battery holder 306 such that backsides of the transmitter and receiver face battery holder 306. After battery holder 306 and holder assembly 242 are coupled together, a potting material may be injected into a cavity between them to attach battery holder 306 and holder assembly 242 together as well as seal the transmitter and receiver within the holder assembly 242 (e.g., backsides of the transmitter and receiver are exposed and attached to the potting material). In some embodiments, a sealing material seals edges of protective material attached to holder assembly 242 and the external exposed surface of the potting material (e.g., potting material exposed from a hole used to inject the potting material between battery holder 306 and holder assembly 242) to protect them from being damaged by contents (e.g., alcohol, acidic beverage, etc.) of a container.

Figure 4:
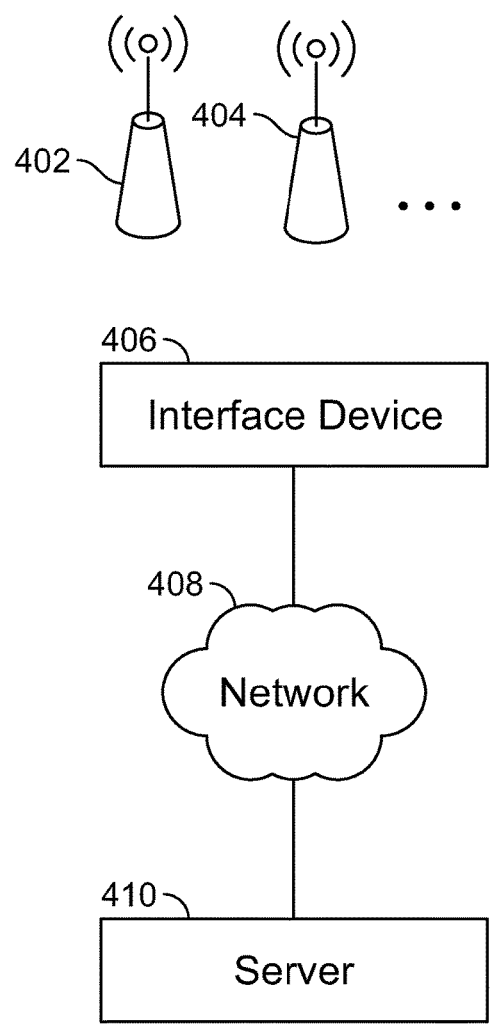
FIG. 4 is a block diagram illustrating an embodiment of a system for an automated container content management environment.

FIG. 4 is a block diagram illustrating an embodiment of a system for an automated container content management environment.

Sensor devices 402 and 404 each include a sensor for automatically determining the amount of content remaining in a container covered by the sensor device. In some embodiments, sensor devices 402 and 404 each include sensor device 100, 200, 300 and/or 350 of FIGS. 1-3B. Although only two sensor devices have been shown in FIG. 4, any number of sensor devices may exist in various embodiments. Examples of sensor devices 402 and 404 include a bottle cap, a bottle cap with a spout, a container lid, and any other container cover configured to cover at least a portion of an opening of a container.

Interface device 406 receives data from one or more sensor devices. For example, sensor device 404 broadcasts an identifier of an amount of content remaining in a container covered by sensor device 404 and interface device 406 receives the identifier for storage and processing. In some embodiments, sensor devices 402 and 404 each need to be configured for a specific type of container to allow each sensor device to be able to more accurately measure the amount of content remaining in a container engaged by the sensor device. For example, the waveform of the ultrasonic signal emitted by a sensor of the container cover is to be specifically configured for the shape/size of the container. In some embodiments, interface device 406 pairs with a sensor device (e.g., via a wireless Bluetooth connection) to transmit configuration data specific to the type of container associated with the sensor device. In some embodiments, a user utilizes interface device 406 to specify the type of container to be associated with a specific sensor device. In some embodiments, a user utilizes interface device 406 to view, manage, and/or configure one or more associated sensor devices. For example, a user utilizes an application of interface device 406 to configure sensor devices, view an inventory of remaining content measured by sensor devices, and automate ordering of low inventory content. Examples of interface device 406 include a mobile device, a smartphone, a smart watch, a wearable computer, a laptop computer, a desktop computer, and any other type of computer. In some embodiments, the interface device is also a charging station for one or more sensor devices. In some embodiments, a charging station includes a mechanism to sanitize a sensor device (e.g., via a suction cleaning, heating, blow drying, etc. mechanism).

In some embodiments, interface device 406 (e.g., base station) acts as a central communication hub for all sensor devices of a user within a certain proximity. In some embodiments, interface device 406 is associated with a specific user. Multiple interface devices may be utilized to manage the same set of sensor devices. For example, multiple interface devices may communicate with one another and/or with a backend server to synchronize data. In some embodiments, interface device 406 includes BLUETOOTH, BLUETOOTH Low Energy, and/or wireless (402.x) protocol-based wireless chipsets. In some embodiments, interface device 406 includes a display to display sensor device status, beverage quantity, recipes, order reminders, etc. In some embodiments, interface device 406 communicates with a Point of Sales (POS) system to correlate sales data with measured content utilization/consumption/depletion.

Interface device 406 is connected to server 410 (e.g., backend server) by network 408. In some embodiments, server 410 remotely stores and/or processes measurement data received from sensor devices. For example, measurement data periodically broadcasted by sensor devices 402 and 404 is received by interface device 406 and interface device 406 provides the received data to server 410 for storage and/or backend server processing. In some embodiments, interface device 406 and/or server 410 utilizes measurement data of a sensor device to calculate an amount of content remaining in a container engaged by the sensor device. For example, a round trip signal reflection time measured by a sensor device is utilized to calculate a percentage fill amount of content remaining in a container. In some embodiments, server 410 processes current and/or historical content measurements to provide analytics (e.g., consumption patterns, determine inventory, analyze cost of goods sold, identify popularity trends, etc.) and inventory management solutions (e.g., inventory forecasting, inventory planning, automated inventory ordering, etc.).

In some embodiments, the system shown in FIG. 4 is utilized in a bar/restaurant environment to automatically track and manage inventory of liquor remaining in liquor bottles. Each liquor bottle is capped using a sensor device that is configured to be a cap for the liquor bottle. In some embodiments, the sensor devices detect the quantity of liquid/beverage remaining in each bottle and broadcast the detected quantity to interface device 406. The interface device reports the received quantity information to server 410. In some embodiments, server 410 provides an online interface to manage container content (e.g., beverage) inventory. For example, a bar/restaurant user entity may access server 410 via an application of interface device 406 and/or a webpage interface provided by server 410 to view and manage inventory of one or more tracked beverage products. Inventory information (e.g., including inventory remaining in open containers measured by sensor devices and full bottle inventory on hand in storage) may be updated automatically and viewed and exported in real time. The inventory of products may be classified by brands, drink type (tequila, whiskey, etc.), recipe (e.g., amount of each mixed drink able to be made using remaining inventory), and/or popularity.

In some embodiments, for a specific user account associated with one or more sensor devices, server 410 learns the consumption pattern, nutrients, and preferences in various types of beverages, flavors, taste, and brands. In some embodiments, using interface device 406, a user is able to access information about consumption quantity, humidity, oxygen content, inventory, drink recipes, and seasonal recommendations associated with current inventory detected using one or more sensor devices. In some embodiments, using interface device 406, a user may access a marketplace to order beverages from various distributors and delivery services. In some embodiments, a user is notified via interface device 406 of a need to replenish an inventory of beverages and may also directly notify one or more distributors to place one or more appropriate orders. In some embodiments, interface device 406 provides recommendations for various drink recipes based on existing inventory detected using one or more sensor devices. In some embodiments, consumption data obtained across a plurality of different user entities may allow trend analysis and manufacturing forecasting across user entities.

In some embodiments, the sensor device includes a mechanism to control and limit an amount of beverage poured via a spout of the sensor device. In some embodiments, the sensor device includes a mechanism to evacuate oxygen out of a container and reseal the container. For example, in order to preserve the freshness of wine, the sensor includes an electronic air pump that pumps air out of a container. In some embodiments, the sensor device includes or has more sensors to detect temperature, humidity, acidity and/or nutrient value of content included in a container. The detected sensor information may be transmitted to an interface device and/or a server (e.g., interface device 406 and/or server 410). In some embodiments, a user is provided a notification when a detected content temperature and/or oxygen level is outside a recommended range.

One or more of the following may be included in network 408: a direct or indirect physical communication connection, mobile communication network, Internet, intranet, Local Area Network, Wide Area Network, Storage Area Network, a wireless network, a cellular network, and any other form of connecting two or more systems, components, or storage devices together. Additional instances of any of the components shown in FIG. 4 may exist. For example, server 410 may be a distributed server and/or may be connected to a plurality of interface devices. In another example, a plurality of interface devices may be utilized to manage and/or utilize the same or different container covers. In some embodiments, components not shown in FIG. 4 may also exist.

Figure 5:
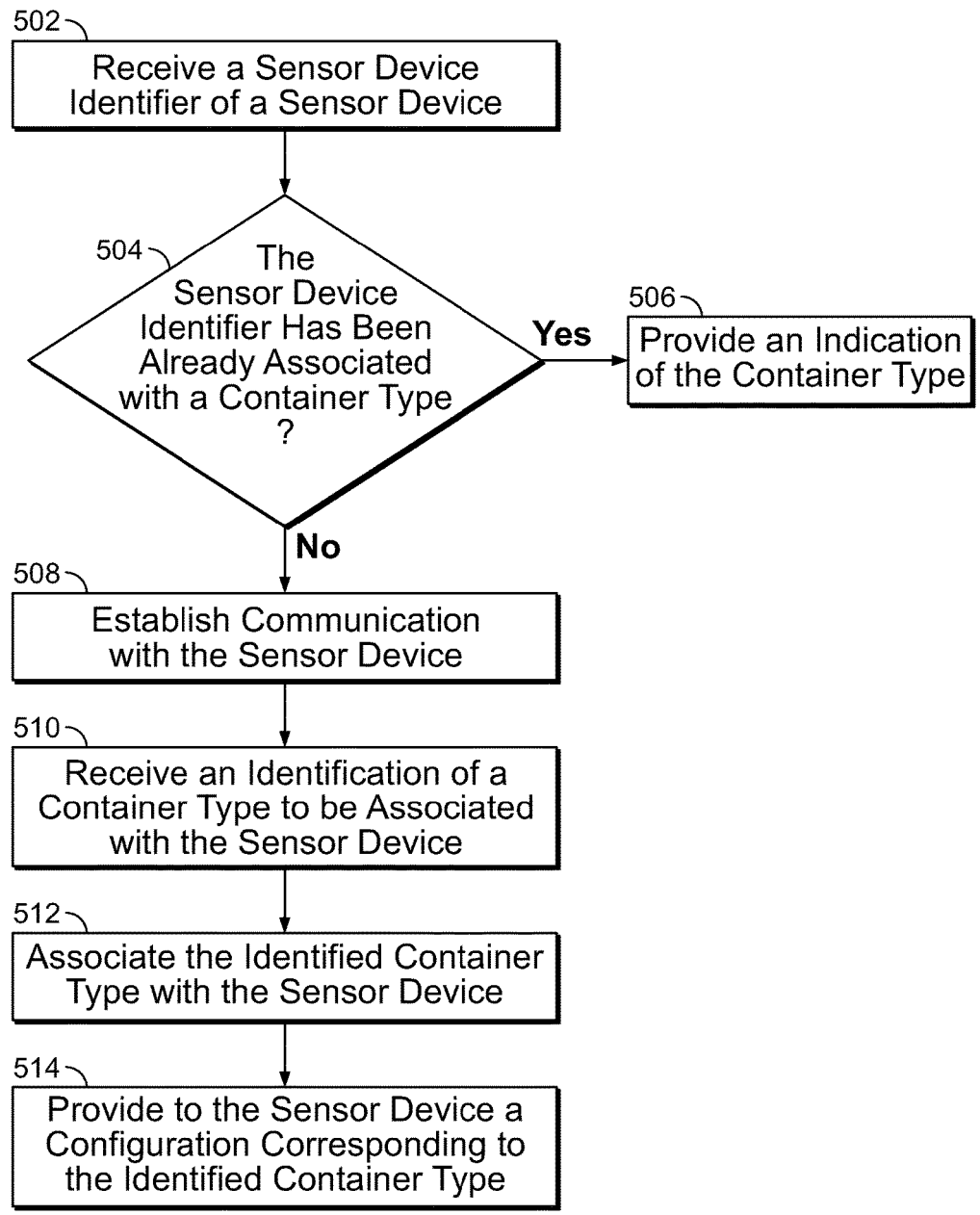
FIG. 5 is a flowchart illustrating an embodiment of a process for providing a configuration for a sensor device.

FIG. 5 is a flowchart illustrating an embodiment of a process for providing a configuration for a sensor device. The process of FIG. 5 may be implemented on interface device 406 of FIG. 4. In some embodiments, the sensor device measures an amount of content included in a container (e.g., sensor device is a bottle cap that measures amount of liquid remaining in a bottle capped by the sensor device) and the sensor device must be configured for a specific container type of the container for the sensor device to be able to more accurately measure the amount of content in the container. For example, various types of containers are shaped differently and the best waveform of the signal utilized to measure the amount of content included in a container may depend on the shape of the container. In some embodiments, a depth measurement provided by the sensor device is translated to a volume and/or percentage measurement value using a shape/volume profile of the container type associated with the sensor device. In some embodiments, the process of FIG. 5 is initiated when a user initiates a sensor device configuration process using an interface device.

At 502, a sensor device identifier of a sensor device is received. In some embodiments, the sensor device is sensor device 100, 200, 300 and/or 350 of FIGS. 1-3B. In some embodiments, the sensor device is sensor device 402 or 404 of FIG. 4. In some embodiments, the sensor device identifier has been wirelessly transmitted by the sensor device. For example, the sensor device broadcasts a unique identifier of the sensor device using a BLUETOOTH (e.g., BLUETOOTH low energy), WiFi, and/or other local or short range wireless communication protocol/signal. In some embodiments, receiving the sensor device identifier includes listening for a signal from a desired type of device (e.g., listen for a signal that is identified as sent by a sensor device). In some embodiments, the sensor device identifier is received via a wired connection. In some embodiments, the sensor device identifier has been transmitted by the sensor device in response to a user indication to the sensor device. For example, when a button on the sensor device is pressed for at least a threshold period of time, the sensor device transmits the sensor device identifier.

At 504, it is determined whether the sensor device identifier has been already associated with a container type. For example, the sensor device has been previously configured for a specific container type at 514 of FIG. 5. In some embodiments, a user desires to know which container type has been already associated with the sensor device. For example, a user may have a plurality of sensor devices that have been each already configured for and capped on a specific type of container. The user may need to remove all of the sensor devices from their associated containers to wash the sensor devices. For example, certain food service health codes may require restaurants/bars to periodically wash bottle cap spouts and sensor devices are configured as bottle cap spouts. However, because each sensor device has been configured for a specific container, once the sensor devices have been washed, the sensor devices may need to be returned back to the correct specific type of container associated with each sensor device. Although one alternative is reconfiguring each sensor device after being washed, the process of reconfiguring each sensor device may be inefficient and cumbersome to perform after each wash as compared to simply returning each sensor device back to the correct specific type of container.

In some embodiments, determining whether the sensor device identifier has been already associated with a container type includes determining whether a storage structure (e.g., table, database, list, etc. stored locally at an interface device and/or remotely at a backend server) includes an entry associating the sensor device identifier with the container type. In some embodiments, determining whether the sensor device identifier has been already associated with a container type includes analyzing information received from the sensor device. For example, the sensor device provides data indicating that the sensor device has been already associated with a container type and configured for the container type.

If at 504 it is determined that the sensor device identifier has been already associated with a container type, at 506, an indication of the container type is provided. For example, an identifier of the container type is displayed on a screen of an interface device to allow a user to return the sensor device back to a container that is of the displayed type. In some embodiments, an indication of the last determined remaining content amount/level determined using the sensor device is provided. For example, there may exist a plurality of containers of the same type and using the content amount/level information, the user is able to return the sensor device back to the identified container type with the identified content level. In some embodiments, an indication is received from a user to reconfigure the sensor device and the process proceeds to 508 (not shown). For example, although the sensor device has been already associated with a container type, a user desires to associate the sensor device with a different container type and the user presses a button on the sensor device to reconfigure the sensor device.

If at 504 it is determined that the identifier has not been already associated with a container type, at 508, communication is established with the sensor device. For example, a wireless communication channel is established. In some embodiments, a BLUETOOTH connection is established. For example, the sensor device is paired with an interface device and the sensor device enters into a paired communication mode.

At 510, an identification of a container type to be associated with the sensor device is received. In some embodiments, the container type identifies a type of container to be covered/capped/engaged by the sensor device. For example, an identification of the specific beverage bottle type to be capped by the sensor device is received.

In some embodiments, the container type identification is received via a user indication. For example, a user selects the container type from a list of container types. In some embodiments, receiving the container type includes receiving an identification of a product and/or packaging to be engaged with the sensor device. For example, a user indicates a product (e.g., liquor product in a specified packaging) to be engaged with the sensor device. In some embodiments, there exists a database of container types for various types of commercially sold beverage packages and the database is utilized to determine a corresponding container type to a user identification of a product.

In some embodiments, receiving the identification of the container type includes receiving a camera image. For example, using a camera of an interface device, a user captures an image of at least a portion of the container to be associated with the sensor device and the image (e.g., an image of a label on a product packaging) is analyzed to automatically determine the container type of the container.

In some embodiments, receiving the identification of the container type includes receiving a barcode/product identifier associated with the container type. For example, using an interface device, a user captures an image of a barcode (e.g., UPC barcode) on the product container to be associated with the sensor device and the image is analyzed to read the barcode identifier of the container. In some embodiments, a container type corresponding to the barcode identifier is identified. For example, the barcode identifier is utilized to search a database that includes entries that associate barcode identifiers with corresponding container types. In some embodiments, the barcode identifier is provided to a server and the server provides a corresponding container type identifier. In some embodiments, there exists a plurality of containers types associated with a barcode/product identifier and a user provides an indication to indicate the specific container type among the plurality of container types associated with the sensor device.

In some embodiments, the sensor device measures a distance between the sensor device and a level of liquid remaining in a container to determine the liquid fill level. For example, a transmitter of the sensor device sends out a signal (e.g., ultrasonic signal) that gets reflected by the surface of the liquid in the container. The reflected signal is detected by a receiver of the sensor device. By measuring the amount of time it took to receive the reflected signal, the distance traveled by the signal before being reflected (e.g., distance between sensor device and liquid surface is half of the total distance traveled by the signal) may be determined by multiplying the amount of time by the speed of the signal (e.g., speed of sound).

In order to correctly determine the amount of content included in the container from the distance information, various parameters of the container must be known. For example, the height of the interior of the container and variations of the cross sectional volume/area of the container across the various depths of the container are needed to calculate the amount/percent of content left in the container. In one example, if the total distance between the bottom of the container and the sensor device is known, the fill height of the container can be determined (e.g., total distance between the bottom and the sensor device minus distance between the sensor device and liquid surface). If the shape and volume of the container are known, the volume of liquid contained in container 102 may be determined. In some embodiments, the container type identification is utilized to obtain a formula/table/database/data structure that maps a measured distance (e.g., fill height, height between liquid surface and sensor device, etc.) to a corresponding remaining content volume/percentage for the specific container type.

At 512, the identified container type is associated with the sensor device. In some embodiments, associating the container type with the sensor device includes storing a data entry (e.g., in a database) that associates the container type with the sensor device identifier. For example, a database of associations between various sensor device identifiers and corresponding associated container types is maintained at an interface device (e.g., device 406 of FIG. 4) and/or a backend server (e.g., server 410 of FIG. 4). This database may also be utilized to store determined content volume/level of containers being tracked by the various sensor devices.

At 514, a configuration corresponding to the identified container type is provided to the sensor device. In some embodiments, a sensor device configuration specific to the identified container type is obtained and provided to the sensor device for configuration. For example, the sensor device needs to be configured for a specific type of container type to enable the sensor device to more accurately measure the amount/level of content remaining in a container. In some embodiments, the configuration corresponding to the identified container type is provided via a communication established with the sensor device in 508.

In some embodiments, the sensor device includes a transmitter for transmitting a signal and a receiver for receiving the signal that has been reflected. The parameters of the signal being transmitted may need to be configured specifically for the container that holds the content to be measured. For example, in order to reduce undesired reflections within the container, the transmitted signal is generated based on the parameters specifically configured for the specific container type. In some embodiments, the configuration specifies a waveform/shape of a signal, a length/width of a signal component (e.g., pulse width), a profile of a signal component, a content of a signal component, a number of pulses in the signal component, a frequency of the signal component, an amplitude/intensity of the signal component, a modulation of the signal component (e.g., pulse-width modulation to be utilized), a duty cycle of the signal component, etc. For example, the signal includes one or more component signal pulses and the configuration specifies the shape/waveform of each signal pulse. In some embodiments, the configuration specifies a number of signal pulses to be transmitted sequentially to measure a content amount/level of a container. In some embodiments, the configuration specifies a configuration of a receiver of the sensor component. For example, a type and/or a parameter of one or more signal filters to be utilized to filter a received reflected signal is specified by the configuration. In another example, automatic gain controller settings/parameters are specified by the configuration.

In some embodiments, the configuration specifies one or more configurable threshold settings to be utilized to detect when a reflect signal has been received by a receiver. For example, a signal transmitted by the transmitter is reflected within a container and the receiver is listening for the reflected signal. However, noise and other factors may cause undesirable signals to be received by the receiver. In order to detect the desired reflected signal that is stronger than the noise, a detection threshold can be adjusted such that a received signal with an amplitude/energy over the threshold is detected as a reflection of the sent signal while a signal with an amplitude/energy below the threshold is ignored as noise. However, given the variance in bottle shape and the transmitted signal, the ideal threshold varies. These variances in the configurable threshold settings may be specified by the provided configuration such that the fill level sensor is able to dynamically adjust the threshold as specified based on the environment of the fill level detection.

In some embodiments, the provided configuration specifies a plurality of different sets of configuration parameters for different fill levels of the container. In some embodiments, one or more sets of configuration parameters are indexed according to a corresponding content level. For example, each set of configuration parameters corresponds to a different range of fill levels of the container. In some embodiments, using a default set of configuration parameters, an initial approximate fill level is determined, and based on the initially determined approximate fill level, a more specific set of configuration parameters corresponding to the initial approximate fill level is utilized to determine a more specific fill level. The default set of configuration parameters may be specific to the specific detected container (e.g., default set of configurations is provided to the sensor device based on the container type) or same across a plurality of different types of containers (e.g., default set is preconfigured into sensor device). In some embodiments, each set of configuration parameters may specify one or more parameters for a signal to be transmitted (e.g., interrogation signal) for reflection off content of the container and/or one or more parameters for receiving and processing the reflected transmitted signal.

In some embodiments, each set of configuration parameters is associated and indexed with a specific range of content fill levels corresponding to when the particular set of configuration parameters is to be utilized. For example, a first set of configuration parameters is to be utilized when a detected fill level is between 0-100 mm (e.g., for a bottom region of the container), a second set of configuration parameters is to be utilized when a detected fill level is between 101-200 mm (e.g., for a middle region of the container), and a third set of configuration parameters is to be utilized when a detected fill level is above 200 mm (e.g., for a top region of the container).

Figure 6:
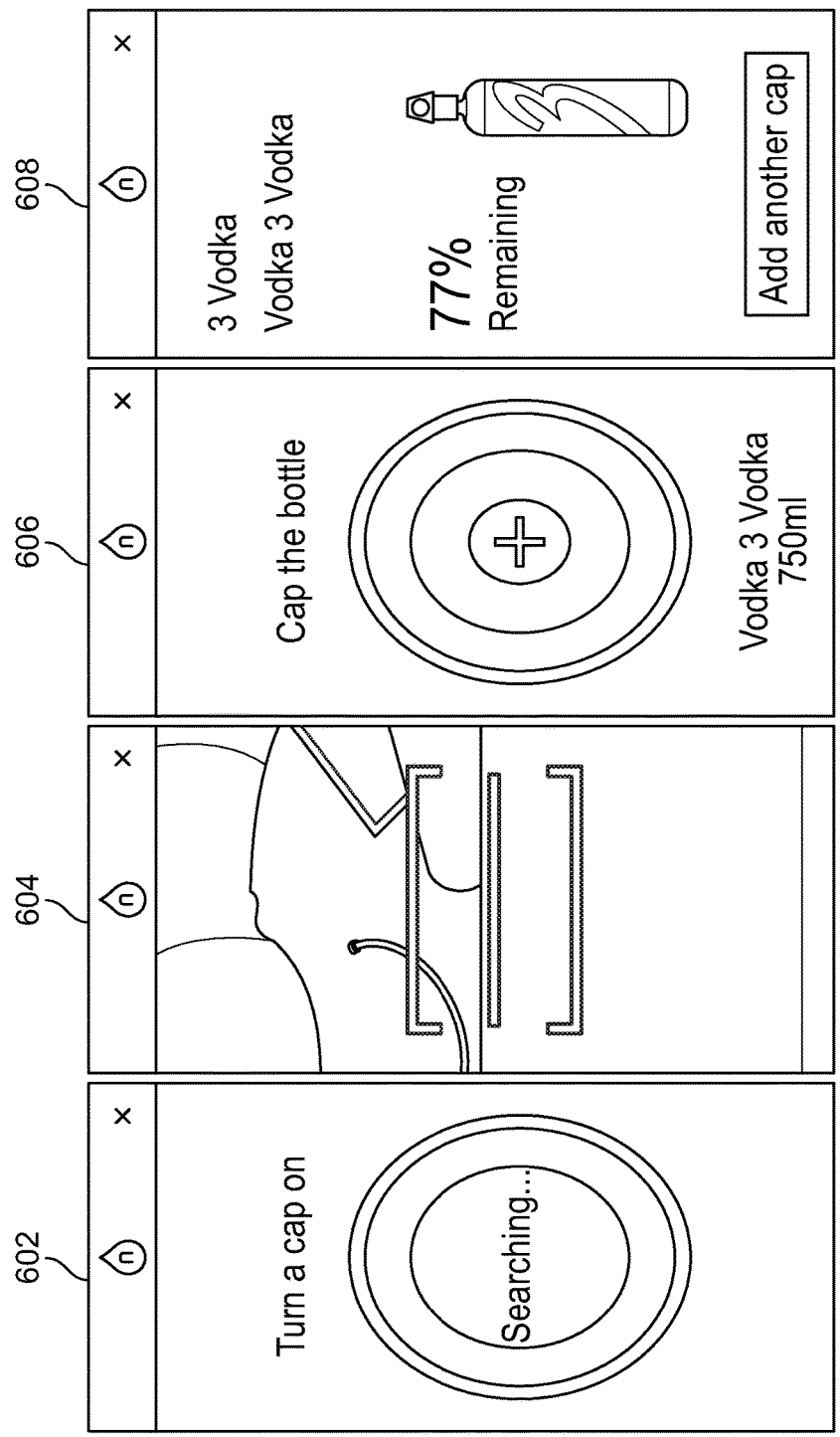
FIG. 6 is a diagram illustrating an embodiment of a user interface for specifying a container type to be associated with a sensor device.

FIG. 6 is a diagram illustrating an embodiment of a user interface for specifying a container type to be associated with a sensor device. In some embodiments, the interface of FIG. 6 is provided on interface device 406 of FIG. 4. In some embodiments, the interface of FIG. 6 is utilized to provide the container type received in 510 of FIG. 5.

Interface screen 602 instructs a user to turn on the sensor device (e.g., by pressing a button on the sensor device for at least a specified period of time, the sensor device turns on and broadcasts its identifier) and the interface device attempts to detect the sensor device (e.g., listens for a new BLUETOOTH LE signal from a sensor device). When the sensor device has been detected, a connection is established with the sensor device (e.g., communication established at 508 and configuration provided in 514 of FIG. 5). Interface screen 604 shows a viewfinder display of a live camera image. Using the displayed viewfinder, a user is to capture an image of a barcode printed on a product container. For example, when a barcode is captured within the shown bracket guidelines, the barcode is read and analyzed to determine whether it is a known barcode that corresponds to a particular container type. Once a valid barcode has been detected, the interface progresses to interface screen 606. In the example shown, interface screen 606 confirms that the barcode has been detected to correspond to container type "3 Vodka 750 ml" that holds vodka contents. A user is instructed to place a sensor device on the container holding the contents to be measured. Once the sensor device has been engaged with the container, a user is to select the "+" icon and the content amount/level of the container is detected. The interface progresses to interface screen 608 where the container type, a representative image of the product, and the latest detected remaining content amount/level (e.g., percentage remaining) are displayed.

Figure 7:
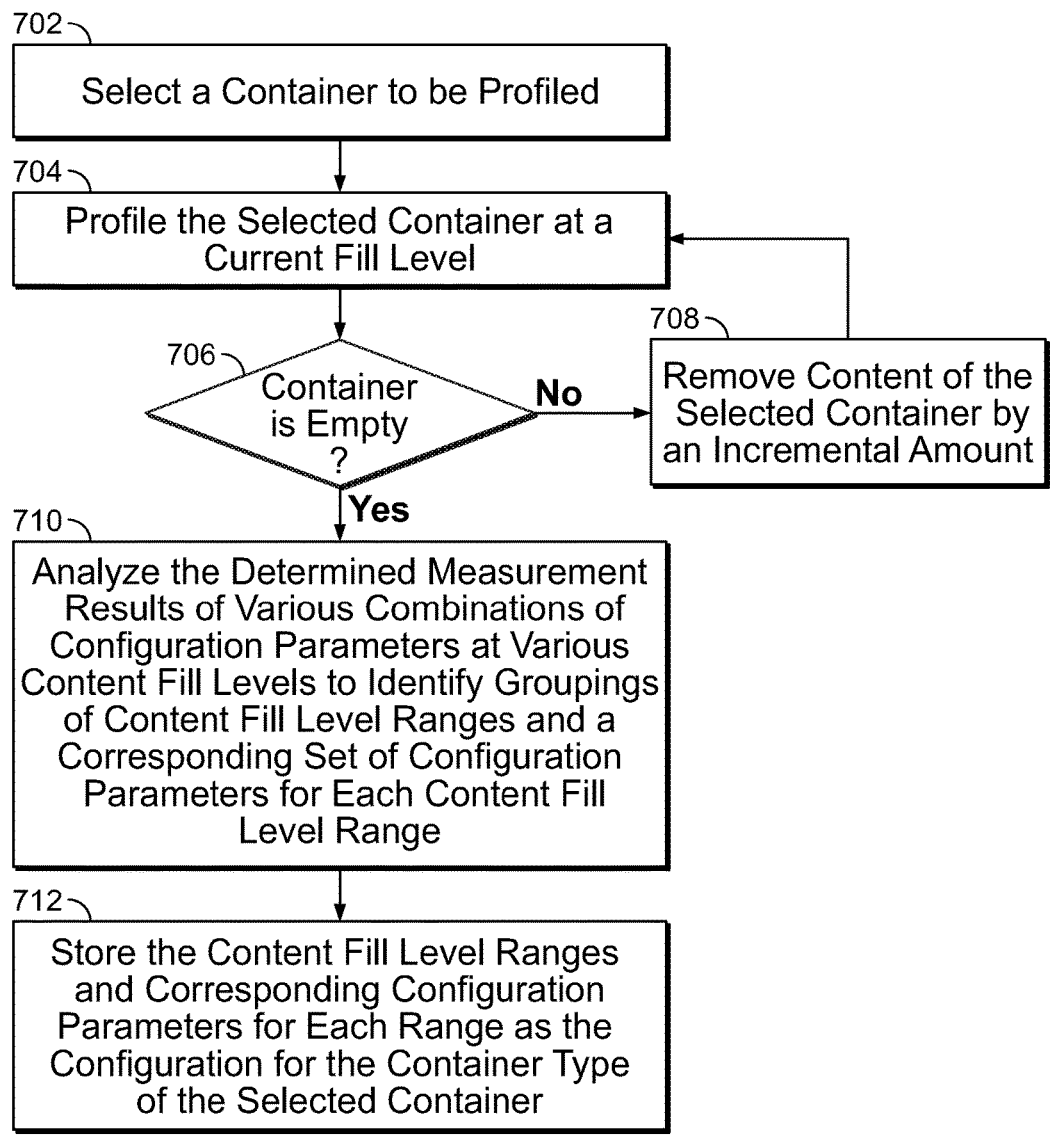
FIG. 7 is a flowchart illustrating an embodiment of a process for determining one or more sets of configuration parameters of a container.
Figure 8:
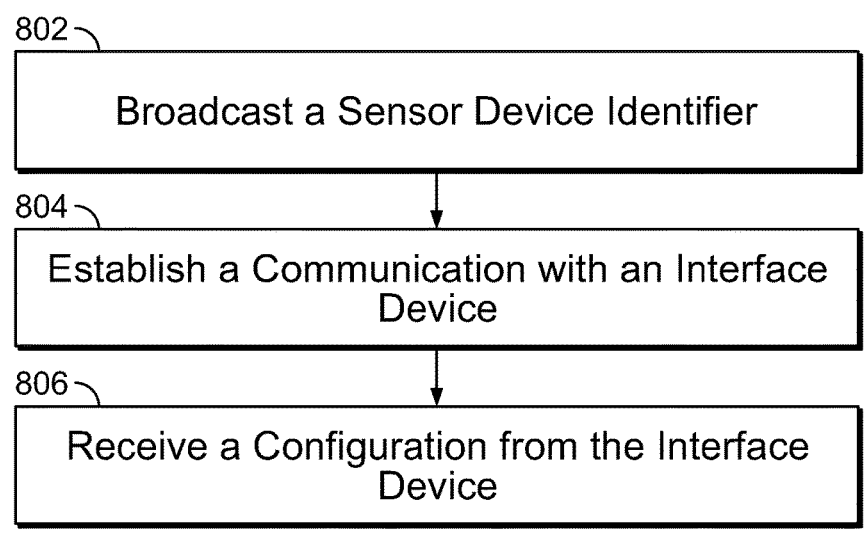
FIG. 8 is a flowchart illustrating an embodiment of a process for configuring a sensor device.

FIG. 7 is a flowchart illustrating an embodiment of a process for determining one or more sets of configuration parameters of a container. For example, the configuration provided in 514 of FIG. 5 and/or received in 806 of FIG. 8 is determined at least in part using the process of FIG. 7. The process of FIG. 7 may be repeated for each different type of container.

At 702, a container to be profiled is selected. For example, a bottle to be profiled to determine its configuration parameters is selected. Selecting the container may include scanning a barcode of the container, capturing a label of the container, selecting/providing an identifier of the container, etc.

At 704, the selected container at a current fill level is profiled. In some cases, the container is initially full and the full container is profiled. In some embodiments, profiling the container includes determining an expected current fill level of the container. For example, an authoritative measuring device is utilized to determine the expected fill level. The authoritative measuring device may be a special measuring device that provides a highly accurate measurement of a depth of the fill level of the container. In some embodiments, the expected current fill level is determined using image processing. For example, an image of the container is captured and the expected fill level of the container is determined by processing the captured image to identify the depth of the fill level captured in the image. In some embodiments, the expected current fill level is determined using a weight scale. For example, a weight of an empty container is known and/or measured and a weight of the current fill level filled container is measured. Based on the difference between these weights and the density of the contents and/or known shape profile of the container, the expected fill level is determined. Once the expected fill level is determined, a configuration of a sensor device (e.g., device 200) that will yield the closest fill level measurement to the expected fill level may be identified by iterating through various combinations of configuration parameters.

In some embodiments, a sensor device (e.g., device 200) is placed (e.g., capped) on the container and the sensor device is configured to iterate through various configuration parameters. For example, measurements are performed using various combinations of interrogation signal parameters and receiver parameters and corresponding measurement results (e.g., identified fill/distance values) of the various combinations are stored. The combinations of various configuration parameters that are varied may include various parameters for one or more of the following of an interrogation signal: a waveform/shape of a signal, a length/width of a signal component (e.g., pulse width), a profile of a signal component, a content of a signal component, a number of pulses in a signal component, a frequency of a signal component, an amplitude/intensity of a signal component, a modulation of a signal component (e.g., pulse-width modulation to be utilized), a duty cycle of a signal component, etc. The combinations of various configuration parameters that are varied may include various parameters for one or more of the following for a signal receiver: an automatic gain control, a variable gain amplifier, a detection threshold, etc. For example, for a given interrogation signal with the same energy, a content reflected signal will be higher in energy (e.g., requiring a higher detection threshold) for a greater fill level as compared to a lower fill level (e.g., requiring a lower detection threshold since a reflected interrogation signal had to travel a greater distance and experienced greater attenuation).

At 706 it is determined whether the container is empty. For example, it is determined whether the container is empty based on the weight of the container.

If at 706 it is determined that the container is not empty, at 708, content of the selected container is removed by an incremental amount. For example, a controlled amount of content is emptied from the container for a next profiling of the container at the new fill level. In some embodiments, the amount of content removed from the container is a preconfigured amount based on a volume, weight, and/or content height. For example, content is removed from the container such that the height of the content within the container drops by 1 mm. In some embodiments, the incremental amount of content is removed automatically. For example, a spout and a valve/pump has been added to the container (e.g., container has been drilled near the bottom of the container and a spout/valve/pump has been added) and the valve and/or pump is automatically controlled to empty a predetermined amount of content. Once the incremental amount of content has been emptied, the process returns to 704 where the new fill level of the container is profiled.

If at 706 it is determined that the container is empty, at 710, the determined measurement results of various combinations of configuration parameters at various content fill levels are analyzed to identify groupings of content fill level ranges and a corresponding set of configuration parameters for each content fill level range. For example, for each profiled content fill level, the various fill level measurement results of the various configuration parameter combinations are sorted and ranked based on closeness to the expected fill level. Then a set of configuration parameters that will result in fill level measurements that are within an acceptable tolerance for a greatest continuous range of fill levels is identified. Then for remaining fill level ranges, a next set of configuration parameters that will result in fill level measurements that are within the accepted tolerance for a greatest continuous range of remaining fill levels is identified. This process of identifying a next set of configuration parameters is repeated until all fill levels have been covered by fill level corresponding configuration parameter sets.

At 712, the content fill level ranges and corresponding configuration parameters for each range are stored as the configuration for the container type of the selected container. For example, at least a portion of the stored configuration is provided in 514 of FIG. 5 and/or received in 806 of FIG. 8 as the configuration for a particular type of container.

FIG. 8 is a flowchart illustrating an embodiment of a process for configuring a sensor device. The process of FIG. 8 may be implemented on sensor device 100, 200, 300 and/or 350 of FIGS. 1-3B.

At 802, a sensor device identifier is broadcasted. In some embodiments, the sensor device identification is the identification received at 502 of FIG. 5. In some embodiments, the sensor device identifier is transmitted in response to entering a pairing mode of the sensor device. For example, the sensor device enters a BLUETOOTH pairing mode to advertise availability of the sensor device for paring. In some embodiments, the sensor device identifier is broadcasted in BLUETOOTH advertising/beacon mode. In some embodiments, a sensor device is first operated in paired mode (e.g., Generic Attribute Profile (GATT) client/server) then switched to advertising/beacon mode. In some embodiments, the sensor device identifier is broadcasted in response to an engagement of a button of the sensor device. For example, when a user presses a button on the sensor device for at least a threshold amount of time, the sensor device enters into a mode that broadcasts the sensor device identification.

At 804, a communication with an interface device is established. In some embodiments, establishing the communication includes establishing the communication established in 508 of FIG. 5. In some embodiments, a BLUETOOTH connection is established. For example, the sensor device is paired with an interface device and the sensor enters into a paired bidirectional communication mode.

At 806, a configuration is received from the interface device. In some embodiments, the received configuration is the configuration provided in 514 of FIG. 5. In some embodiments, the received configuration specifies one or more parameters of an interrogation signal that is to be reflected off contents within a container to measure an amount and/or fill level of content included in the container. In some embodiments, the configuration specifies one or more parameters of a receiver of the received reflected interrogation signal. In some embodiments, the configuration specifies one or more reflection detection thresholds.

In some embodiments, the configuration specifies one or more parameters of a filter to apply to the received reflected interrogation signal. In some embodiments, the configuration specifies one or more parameters of an automatic gain controller of the receiver. In some embodiments, the configuration includes an identifier of a profile that has been already stored in a data storage of a sensor device.

In some embodiments, the received configuration specifies a plurality of different sets of configuration parameters. For example, each set corresponds to a different fill level of the container (e.g., each set indexed to a range of fill levels). In some embodiments, using a default set of configuration parameters (e.g., default set of configuration parameters is included in the received configuration), an initial estimated fill level is determined and based on the initial estimate of the fill level, a more specific set of configuration parameters included in the received configuration is identified to be utilized to determine a more accurate fill level.

In some embodiments, each set of configuration parameters identified by the received configuration specifies one or more signal parameters to generate a distinct interrogation signal corresponding to the set. For example, each set of configuration parameters specifies one or more of the following parameters of a signal to be transmitted: a waveform/shape of a signal, a length/width of a signal component (e.g., pulse width), a profile of a signal component, a content of a signal component, a number of pulses in a signal component, a frequency of the signal component (e.g., changing a frequency of an input signal to a speaker changes a spectrum of frequencies outputted by the speaker), an amplitude/intensity/energy of a signal component, a modulation of a signal component (e.g., pulse-width modulation to be utilized), a duty cycle of a signal component, etc. In some embodiments, each set of configuration parameters is identified/indexed for use for a specified range of container fill levels. For example, because the shape of the empty portion of the container (e.g., contributing to different reflection patterns) and a distance an interrogation signal must travel may vary with the fill level of the container, a different interrogation signal, detection threshold and/or receiver setting is to be utilized for various different fill levels and the signal parameters of these different interrogation signals are specified as different sets of configuration parameters. In some embodiments, the same interrogation signal may be utilized for a particular container regardless of fill level.

In some embodiments, the interrogation signal is shaped to produce an interrogation signal that will result in a received signal with signal properties for more accurate and consistent threshold detection to detect reflections of the interrogation signal. In some embodiments, the interrogation signal is shaped to produce an interrogation signal that will result in a received signal with a narrow peak for more accurate and consistent peak detection of a received reflected signal. When multiple pulses are included in the interrogation signal, a received signal is a convolution of the received signal components of the pulses. This resulting signal may be shaped by varying the number, amplitude, width, etc. of the pulses to produce a narrow peak (e.g., correlation peak for detecting time/length interrogation signal travels to determine fill level). For example, pulse-width modulation to be performed is specified by a received set of configuration parameters.

In some embodiments, although a manufacturer/vendor specification of a speaker to be utilized to transmit an interrogation signal specifies a minimum energy of an input signal to the speaker, a configuration parameter specifies a signal energy that is lower than the specified rated energy of the speaker manufacturer/vendor. For example, although a manufacturer specifies that 6 volts is the rated voltage that should be provided to a speaker, a voltage between 2-2.8 volts is specified by a configuration parameter to be provided to the speaker. In another example, a voltage as low as 1 volt is supplied to the speaker.

In some embodiments, the received configuration specifies configuration parameters of a signal receiver. For example, parameters of an automatic gain control, a variable gain amplifier, a detection threshold, etc. are specified in the received configuration for receiving and processing a reflected interrogation signal. In some embodiments, the received configuration specifies a plurality of different sets of receiver configuration parameters. For example, each set of receiver configuration parameters corresponds to a different current fill level (e.g., range) of the container (e.g., different receiver configuration parameters corresponding to different sets of interrogation signal configuration parameters of the various different fill level ranges).

Figure 9:
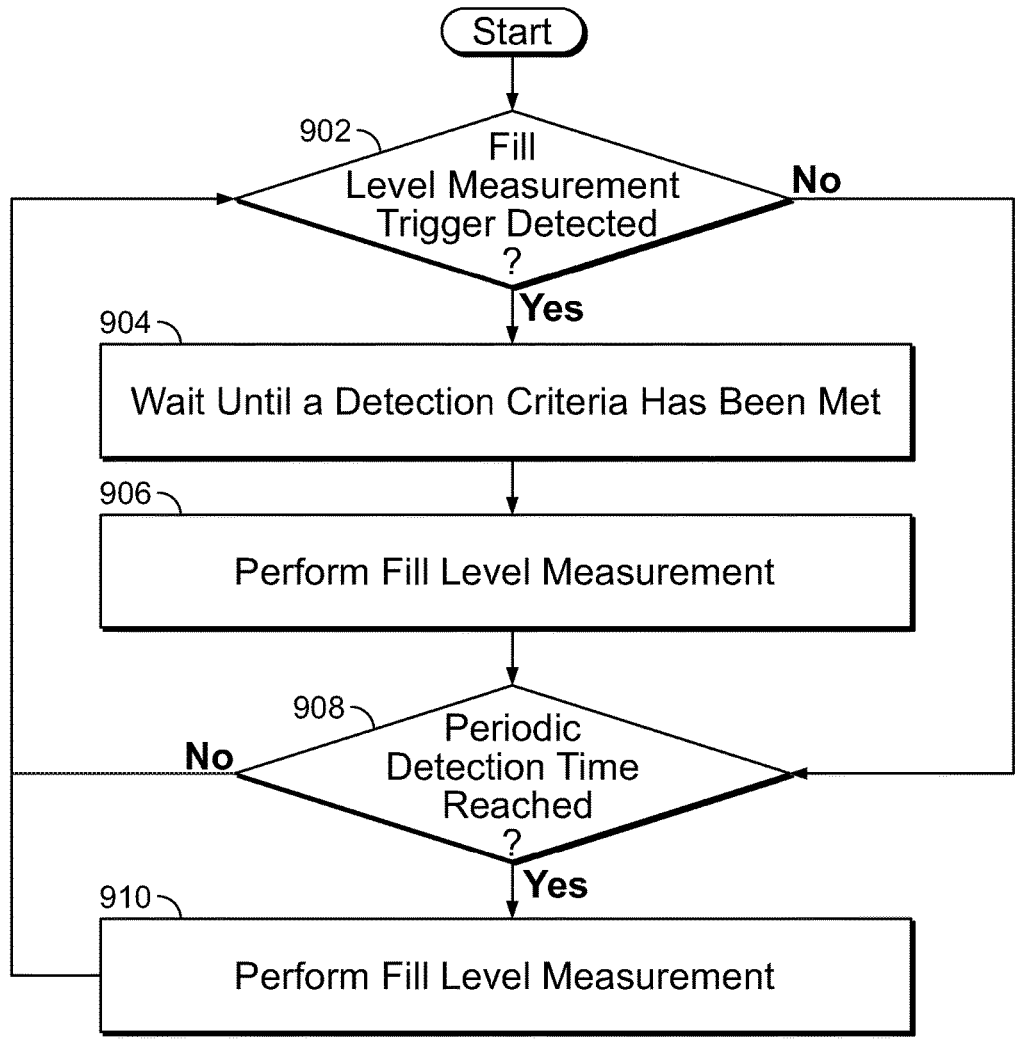
FIG. 9 is a flowchart illustrating an embodiment of a process for detecting a fill level of a container using a fill level sensor.

FIG. 9 is a flowchart illustrating an embodiment of a process for detecting a fill level of a container using a fill level sensor. The process of FIG. 9 may be implemented on sensor device 100, 200, 300 and/or 350 of FIGS. 1-3B. At least a portion of the process of FIG. 9 may be continually performed to detect an updated fill level of a container.

At 902, it is determined whether a fill level measurement trigger is detected. For example, an accelerometer, a motion detector, an orientation sensor, or another detector/sensor included in a fill level sensor device that detects movement and/or an orientation of the fill level sensor device detects a triggering condition to start fill level measurement. In some embodiments, data provided by an accelerometer, a motion detector, and/or an orientation sensor is received and analyzed to detect whether a detected movement meets a specified threshold to trigger a fill level measurement. For example, it is determined whether a magnitude of a detected movement is at least a threshold amount of distance, time, and/or angle. By using the trigger to initiate the fill level measurement, the device can be placed in a low power state to conserve power while waiting for the trigger.

If at 902 it is detected that the fill level measurement trigger is detected, at 904, the process waits until a detection criteria has been met. For example, the measurement trigger may have been caused movement associated with pouring content out of a spout of the device and in order to obtain an accurate measurement, a wait time is needed to ensure that the liquid content of the container has settled from the movement.

In some embodiments, the detection criteria specifies an orientation criteria. For example, before fill level measurement is to be performed, an accelerometer, gyroscope, and/or orientation sensor must indicate that the fill level sensor is in the proper orientation associated with performing an accurate fill level measurement. In one example, while a user is still tipping the sensor and the container upside down to pour contents out of the spout of the device, the device cannot properly measure the fill level and the detection criteria has not been met. In another example, if the user has uncapped the fill level sensor from the container and lays the fill level sensor down on its side on a table, the sensor device is detected as not being in the desired upright orientation and the detected criteria has not been met.

In some embodiments, the detection criteria specifies a movement criteria. For example, before the fill level measurement is to be performed, an accelerometer, gyroscope, and/or orientation sensor must indicate that the movement/position of the fill level sensor device is relatively stable (e.g., detected movement within specified period of time is within a specified range or below a threshold). In one example, if the device is still in the process of being moved, an accurate fill level measurement cannot be achieved due to movement of contents within the container.

These detection criteria in combination may specify that in order to meet the detection criteria, the fill level sensor must be oriented upright and movement stable for at least a set period of time. In some embodiments, if the detection criteria is not met for at least an error threshold amount of time and/or an error is detected, an error/message is provided (e.g., provided to server 410 of FIG. 4 and/or user) to allow a user to correct the error (e.g., user forgot to cap the container using the sensor device after pouring contents out of the container and a reminder is provided to the user after a preconfigured amount of time to put the sensor device back on the container).

At 906, a fill level measurement is performed. For example, an interrogation signal is sent and its reflection is detected and analyzed to determined content fill level of a container engaged to the fill level sensor device. In various embodiments, at least a portion of the process of FIG. 10 is utilized to perform the fill level measurement.

At 908, it is determined whether a periodic detection time has been reached. Rather than only relying on the fill level measurement trigger, a fill level measurement is performed periodically to ensure correct fill level detection and it is determined whether it is time to perform a periodic fill level measurement. For example, errors detecting the fill level measurement trigger and/or detecting incorrect fill levels may be corrected by periodically performing a fill level measurement. The amount of time between periodic detection may be regular intervals and/or based on dynamic factors. For example, periodic detection time is reached periodically every set amount of time (e.g., every ten minutes). In another example, periodic detection time is reached after a set amount since a previous fill level measurement (e.g., set amount of time after triggered measurement). In some embodiments, the periodic detection time is dynamically adjusted based on one or more of the following: time of day, day of week, battery power, magnitude of variances in previous measurements, sensor data, etc. In an alternative embodiment, periodic detection is optional and/or not performed.

If at 908 it is determined that the periodic detection time has been reached, at 910, fill level measurement is performed. For example, an interrogation signal is sent and its reflection is detected and analyzed to determine content fill level of a container engaged to the fill level sensor device. In various embodiments, at least a portion of the process of FIG. 10 is utilized to perform the fill level measurement.

Figure 10:
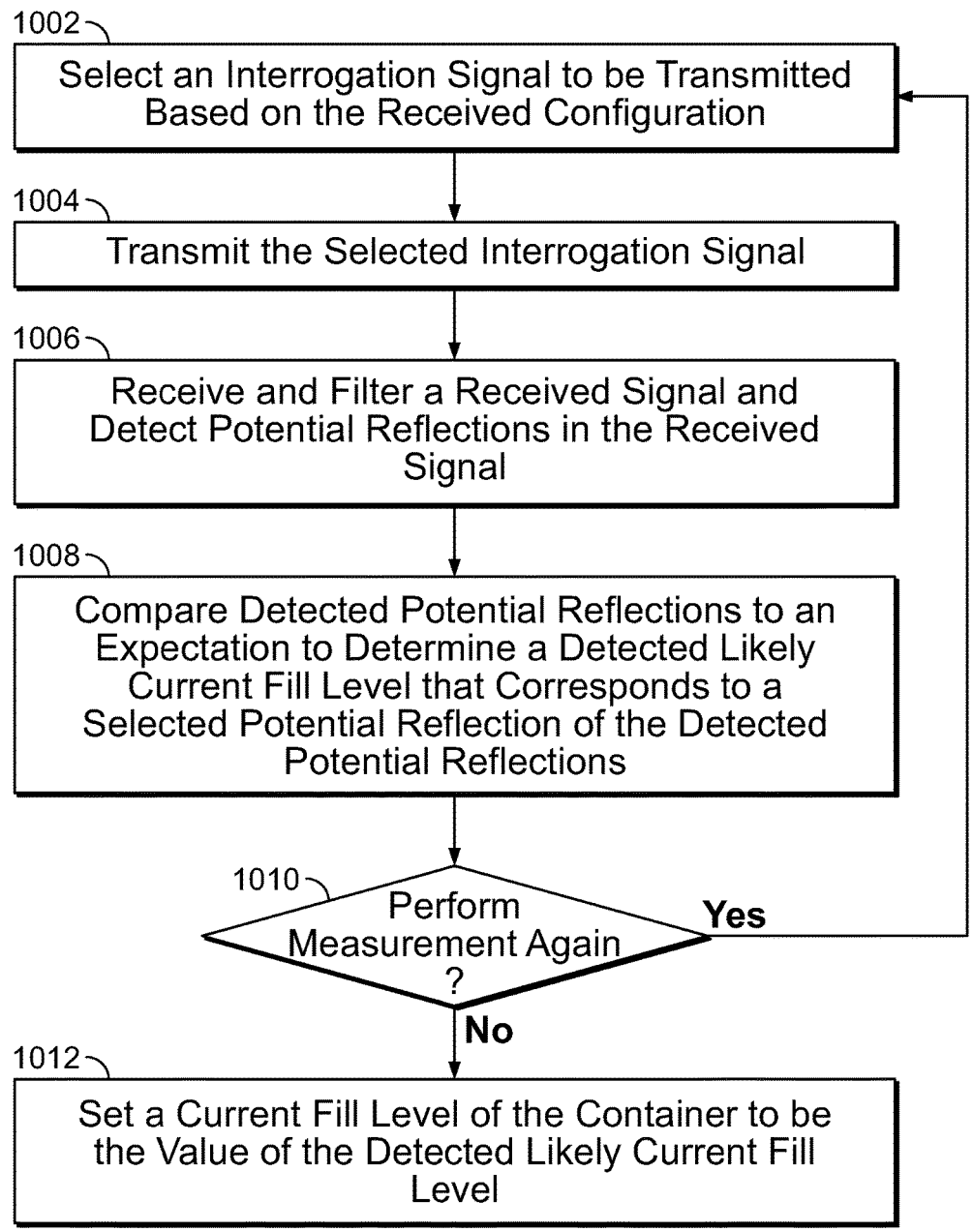
FIG. 10 is a flowchart illustrating an embodiment of a process for measuring a fill level of a container using a fill level sensor device.

FIG. 10 is a flowchart illustrating an embodiment of a process for measuring a fill level of a container using a fill level sensor device. The process of FIG. 10 may be implemented on sensor device 100, 200, 300 and/or 350 of FIGS. 1-3B. In some embodiments, at least a portion of the process of FIG. 10 is included in 906 and/or 910 of FIG. 9.

At 1002, an interrogation signal to be transmitted is selected based on a received configuration. For example, the configuration received in 806 of FIG. 8 specifies a default set of configuration parameters of a default interrogation signal to be utilized to determine an initial approximate fill level. The received configuration may also specify one or more fill level range specific sets of configuration parameters that specify the specific interrogation signal to be utilized for a particular fill level. For example, for each range of fill levels, a different set of configuration parameters for a specific interrogation signal to be utilized for the particular fill level range is specified in the received configuration. In one example, once an initial approximate fill level is determined using the default set of configuration parameters, a specific set of configuration parameters corresponding to a specific fill level range that includes the initial approximate fill level is selected as the configuration parameters of the interrogation signal to be utilized to determine a more specific fill level. In some embodiments, the received configuration specifies a plurality of sets of configuration parameters and each set is utilized to generate and transmit a corresponding interrogation signal one or more times until a set that results in a consistent fill level measurement has been identified. This set of configuration parameters that resulted in the consistent fill level measurement may be utilized for subsequent measurements of different fill levels and/or this search for a consistent result producing set of configuration parameters may be performed periodically and/or each time a fill level measurement is performed. In some embodiments, the measurement fill level of the identified set is utilized to select the set of configuration parameters to be utilized to determine a more accurate fill level. For example, the set of configuration parameters for the fill level range corresponding to the measured fill level is selected.

In some embodiments, based on a previous fill level, the interrogation signal to be transmitted is identified. For example, a previously utilized interrogation signal (e.g., corresponding to a previously selected set of configuration parameters) is selected for use unless a previously determined fill level indicates that another interrogation signal (e.g., corresponding to another set of configuration parameters) should be utilized (e.g., a next fill level range interrogation signal is selected because a previously determined fill level is at the limit of or beyond the valid fill level range of the previously utilized interrogation signal).

In some embodiments, the interrogation signal is consistent across all fill levels of the container. For example, although the interrogation signal is specific to a particular type of container, the interrogation signal is consistent for all fill levels of the container. In some embodiments, the interrogation signal is an impulse. In some embodiments, the interrogation signal is an acoustic signal. In some embodiments, the interrogation signal is an ultrasonic signal.

At 1004, the selected interrogation signal is transmitted. In some embodiments, the transmitted interrogation signal is generated using a selected set of configuration parameters within the received configuration. In some embodiments, the selected interrogation signal includes one or more signal pulse components specified by the selected set of configuration parameters. For example, each signal pulse may be identical and the signal pulses are emitted sequentially with an optional period of no signal (e.g., silence) between the signal pulses.

The number of signal pulses, the length of the signal pulses, a frequency of the signal pulses, a signal content of the signal pulses, a strength/magnitude of the signal pulses, a profile of the signal pulses, a waveform of a signal pulse, a length of null signal between the signal pulses, a length/width of a signal component, a pulse width, an amplitude/intensity of the signal component, a modulation of the signal component (e.g., pulse-width modulation to be utilized), and/or a duty cycle of the signal component, etc. may be specified by the received configuration.

The variations of the interrogation signal may be due to the type of container that is holding the content to be measured and/or fill level range of the container. For example, the thickness of the container, the material of the container, a shape of the container, a length of the container, a width of the container, a size of the container, and/or an amount/type of the content included in the container may all affect how and where the interrogation signal travels and bounces within the container and the received configuration is specific to the container type and/or fill level of the container to improve the content amount/volume/level measurement of a sensor device.

In some embodiments, the interrogation signal is consistent across all fill levels of the container. In some embodiments, the interrogation signal is an impulse generated by a speaker. In some embodiments, the interrogation signal is an acoustic signal. In some embodiments, the interrogation signal is an ultrasonic signal.

In some embodiments, by measuring the amount of time it takes for the interrogation signal to travel from a sensor device engaged at the top of the container to content (e.g., liquid) remaining within the container and reflect back to the sensor device, the distance traveled by the interrogation signal before being reflected (e.g., distance between sensor device 100 and liquid surface is half of the total distance traveled by the signal as shown in FIG. 1) may be determined by multiplying the amount of time by the speed of the signal (e.g., speed of sound when the interrogation signal is an ultrasonic signal). If the total distance between the bottom of the container and the sensor device is known, the fill height of the container can be determined (e.g., total distance between bottom and sensor device minus distance between sensor device and content surface). If the shape and volume of the bottle are known, the volume/amount of content contained in the container may be determined.

At 1006, a receiver receives a received signal, the received signal is filtered, and potential reflections are detected in the received signal. For example, the interrogation signal is reflected in the container in various surfaces and directions and the reflections are detected by the receiver as the received signal that includes components from the various reflected signals. The received signal is filtered to improve signal to noise ratio and the signal reflections detected in the received signal are identified.

In some embodiments, filtering the received signal includes isolating the desired signal (e.g., band-pass filter the received signal) to a desired frequency range and amplifying the signal. In some embodiments, a predetermined beginning portion (e.g., predetermined amount of time in the beginning of the signal) of the received signal may be modified/muted/ignored to ignore signal contents that was detected due to coupling between the transmitter and receiver of the sensor device. For example, when the transmitter transmits the interrogation signal, the signal may be received by the receiver of the sensor device (e.g., conducted directly from the transmitter to the receiver via the housing of the sensor device) before the signal is reflected by the contents of the container, and this undesired signal portion received in the beginning of the received signal is not to be identified as a reflection.

The configuration received in 806 of FIG. 8 may specify the parameters/configuration of the filter, amplification, analysis, modification, etc. For example, parameters of an automatic gain control, a variable gain amplifier, a detection threshold, etc. are specified in the received configuration. In some embodiments, the received configuration specifies a plurality of different sets of receiver configuration parameters. For example, each set of receiver configuration parameters corresponds to a different fill level range of the container (e.g., matching different sets of interrogation signal configuration parameters of the fill level range, matching a default interrogation signal, etc.). In some embodiments, the filtering/detection parameters corresponding to the selected interrogation signal are selected and utilized in processing the received signal.

Detecting the potential reflections includes analyzing the received signal to identify one or more potential reflections of the transmitted interrogation signal detected in the received signal. For example, not only does the transmitted interrogation signal directly reflect off contents in the container to measure the fill level, the transmitted interrogation signal bounces off container contents at other non-direct angles as well as off walls of the container and other components of the fill level sensor device as the interrogation signal spreads out and bounces multiple times. However a detected potential reflection may not be actually due to a reflection. For example, a detected potential reflection may be an artifact of noise or detection error. The potential reflections are to be analyzed to select the potential reflection that corresponds to a fill level of the container.

Each received reflection of the interrogation signal that reaches the receiver may be characterized by an increase in signal amplitude corresponding to when the reflected signal reaches the receiver. In some embodiments, identifying the potential reflections includes identifying each instance in the received signal when the signal strength meets a detection threshold. For example, reflections are identified by detecting instances in the received signal where the amplitude increases to transition from being below the detection threshold to meet the threshold. The detection threshold may be dynamically set and the detection threshold was identified in the configuration received in 806 of FIG. 8. In some embodiments, detecting the potential reflections includes identifying locations/times in the received signal that correspond to when the amplitude of the received signal meets the detection threshold from an amplitude that is below the detection threshold. Each identified potential reflection is recorded as a time value (e.g., travel time of the associated reflected signal of the reflection) and/or a distance value (e.g., travel distance of the associated reflected signal of the reflection).

In some embodiments, if an error is detected by the fill level sensor device during fill level measurement, the process ends and an indication of the error is provided. For example, detected errors such as detected movement during fill level measurement, not proper fill level sensor positioning/latch to container, blocked receiver/sensor (e.g., liquid beaded on sensor or receiver and is hindering the detection), etc. are indicated and the process stops to allow a user to correct the error.

At 1008, detected potential reflections are compared to an expectation to determine a detected likely current fill level that corresponds to a selected potential reflection of the detected potential reflections. For example, because multiple potential reflections are likely detected in the received signal, one of the potential reflections is to be selected as the potential reflection that corresponds to a direct reflection of the interrogation signal from contents of the container. In some embodiments, comparing the potential reflections includes comparing a reference fill level to a corresponding fill level of each detected potential reflection. For example, the corresponding fill level of each detected potential reflection is the fill level that corresponds to selecting the corresponding detected potential reflection as the desired reflection of the interrogation signal from contents of the container in determining the fill level of the container. Comparing the expected fill level to a corresponding fill level of each detected potential reflection may include determining a difference between the reference fill level and the corresponding fill level.

In some embodiments, the fill level includes a distance/length value. For example, each detected potential reflection identifies an amount of time between transmitting the interrogation signal and receiving the portion of the signal corresponding to the detected potential reflection, and a distance traveled by the reflected signal of the potential reflection is determined. In some embodiments, the fill level is associated with a fill height. For example, if the total distance between the bottom of the container and the fill level sensor device is known, the fill height of the container can be determined (e.g., total distance between bottom and sensor device minus distance between sensor device and liquid surface). In some embodiments, the fill level includes a volume value. For example, a table/database/data structure that maps fill length/distance (e.g., distance between content/liquid surface and sensor device, etc.) to content/liquid volume of the container is utilized to determine content/liquid volume corresponding to the determined fill height/distance. Different tables/databases/data structures may exist for different types of containers and data specific to the container is received in 806 of FIG. 8.

In some embodiments, the expectation corresponds to a reference/expected fill height/distance and/or reference/expected amount of content remaining in the container based on a previously detected fill level (e.g., previously determined in 1008 at a previous iteration). For example, amount/level of content that is typically removed from the container within a certain time period or instance is usually within a range from the previous fill level (e.g., amount of liquid content poured from a spout of the fill level measurement device is typically constant for each pour). The expectation may be associated with this range such that the potential reflection that corresponds to a fill level within the range is selected as the detected likely current fill level. Determining the detected likely current fill level may include selecting the reflection/fill level candidate of the potential reflections that is closest to the expectation. For example, the potential reflection corresponding to a fill level within the specified range is to be selected if available and if no potential reflection corresponds to the fill level within the specified range, a potential reflection outside the range but closest to the range is to be selected.

In some embodiments, the expectation is based on a reference fill level (e.g., previously determined fill level). In some embodiments, the reflection corresponding to a minimal change in fill level from the previously determined fill level is to be selected and each fill level corresponding to each of the detected potential reflections is compared (e.g., to determine difference) with the reference fill level to find the reflection that is closest to the reference fill level (e.g., find candidate fill level that corresponds to smallest difference from previously current fill level). If a previously determined fill level does not exist (e.g., first time measuring fill level), the potential reflection corresponding to the largest fill level (e.g., reflection associated with smallest time/distance traveled or largest amount of content in container) is selected. The detected likely current fill level that corresponds to the selected reflection may be a larger fill level than the previous current fill level (e.g., container refilled, previous fill level measurement was incorrect, etc.). The fill level corresponding to the selected reflection is selected as the detected likely current fill level.

At 1010, it is determined whether the measurement is to be performed again. For example, the fill level measurement is to be performed again if the detected likely current fill level does not meet the expectation. Various factors such as liquid/content settling time and other causes of signal noise may have caused an error in reflection detection and the fill level measurement is to be performed again to verify the earlier measurement result. In some embodiments, if it is determined that the measurement is to be performed again, an indicated current fill level of the container is maintained at a previous fill level and not set as the new detected likely current fill level until the new detected fill level can be verified with the repeat measurement.

In some embodiments, determining whether to perform the measurement again includes determining whether an error has been detected during an earlier measurement and determining to perform the measurement again if one or more certain types of errors have been detected. For example, it is expected that the container and the fill level sensor device are not physically moved during fill level measurement (e.g., movement may disturb contents inside the container and the contents may have been moving when the measurement was performed). When an error is detected by the sensor device (e.g., using data from an accelerometer, gyroscope, orientation sensor, signal received, etc.) during the fill level measurement, the error is indicated as a flag associated with the measurement and based on the indicated flag, it is determined to perform the measurement again.

In some embodiments, determining whether to perform the measurement again includes determining whether the detected fill level in 1008 is within the expectation. For example, it is determined whether the detected fill level is within a specified value difference range from a previously determined to be current fill level. The value difference range may be a range from a negative difference to a positive difference (e.g., if the container is not expected to be refilled, a negative difference limit of the range is greater than the positive difference limit of the range because content is expected to be consumed while the positive difference limit allows minor variation in measurements to be tolerated). In some embodiments, if the detected fill level is outside the expectation, it is determined to perform the measurement again while if the detected fill level is within the expectation, it is determined to not perform the measurement again.

In some embodiments, in the event the detected fill level in 1008 was determined in response to the determination in 1010 to perform the fill level measurement again and the new detected likely current fill level is the same or within a threshold difference from the earlier detected fill level (e.g., the fill level measurement that caused a new measurement to be performed), it is determined to not perform the measurement again in 1010. For example, despite the new detected fill level being outside an expected range, if the new detected fill level confirms the earlier detected fill level, the fill level measurement is not to be repeated. In some embodiments, in the event the repeated measurement produces a new detected fill level that is substantially different than the earlier detected fill level, it is determined in 1010 to repeat the measurement again. If repeated measurements do not produce a stable measurement within a specified number of repeated measurements, a measurement error may be provided and the process ends. In some embodiments, in the event the repeated measurement produces a new detected fill level that is substantially different than the earlier detected fill level but the new detected fill level meets the expectation, it is determined to not repeat the measurement again and accept the new detected fill level.

If at 1010 it is determined to perform the measurement again, the process returns to 1002 to repeat the fill level measurement. In some embodiments, in performing the repeat measurement, a different interrogation signal may be utilized from the previous measurement. For example, a more specific interrogation signal corresponding to the fill level range of the previous measurement is to be utilized (e.g., different set of configuration parameters selected for the interrogation signal based on the previous measurement). In some embodiments, the same interrogation signal is utilized.

If at 1010 it is determined to not perform the measurement again, at 1012, a current fill level of the container is set to be the value of the detected likely current fill level. For example, the detected fill level and/or associated content volume is provided by the fill level sensor device (e.g., along with an identifier of the fill level sensor device) to interface device 406 that updates a server stored record of the fill level and/or content volume of the container measured by the fill level sensor device. In some embodiments, the detected fill level is associated with one or more indications (e.g., error indications, warning indications, etc.) regarding the detected fill level measurement and/or status of the fill level sensor device and the one or more indications are provided.

Figure 11:
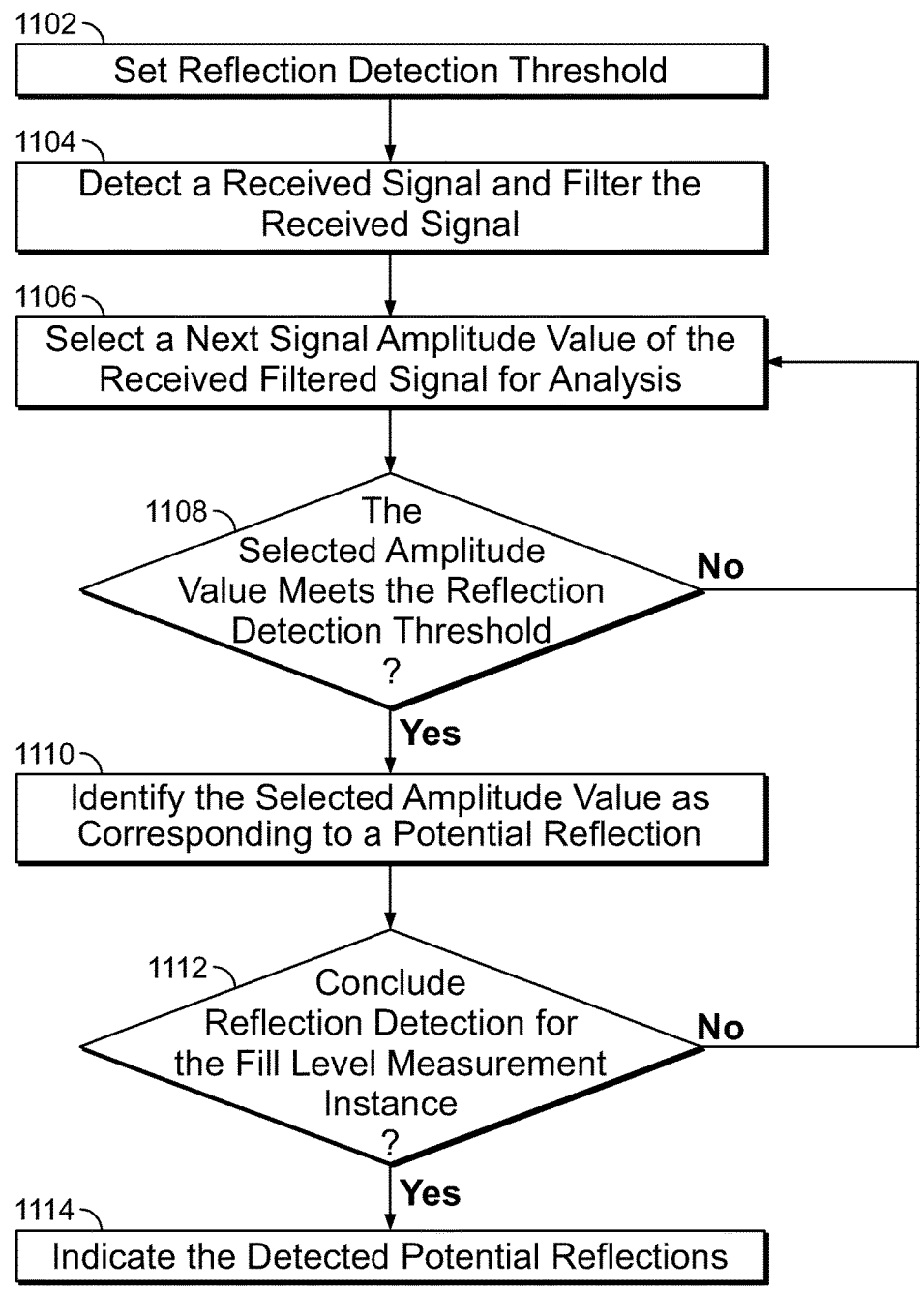
FIG. 11 is a flowchart illustrating an embodiment of a process for detecting potential reflections indicated by a received signal.

FIG. 11 is a flowchart illustrating an embodiment of a process for detecting potential reflections indicated by a received signal. The process of FIG. 11 may be implemented on sensor device 100, 200, 300 and/or 350 of FIGS. 1-3B. In some embodiments, at least a portion of the process of FIG. 11 is included in 1006 of FIG. 10.

At 1102, a reflection detection threshold is set. In some embodiments, a potential reflection is detected in a received signal of the sensor device when a signal amplitude of the signal reaches the detection threshold. For example, a reflection is detected when a received signal amplitude increases to meet the reflection detection threshold. The detection threshold may be dynamically varied based on a type of container that includes the content to be measured and/or a fill level of the container. For example, the shape of the container and the amount of distance that an interrogation signal has to travel to detect the fill level may influence the strength of the reflected signal that is received at the receiver of the fill level sensor and the detection threshold is adjusted and set based on one or more factors. In some embodiments, specification of the detection threshold was received in 806 of FIG. 8. For example, based on a type of container to be associated with the fill level sensor, one or more detection thresholds specific to the particular container are provided to the fill level sensor device during fill level detection. In some embodiments, the detection threshold is at least based on a previously detected fill level of the container and a previously determined fill level and/or estimated fill level of the container is utilized to select the reflection detection threshold. For example, for different ranges of fill levels, a different detection threshold is to be utilized and the detection threshold corresponding to the last measured fill level is selected to be utilized. In various embodiments, the reflection detection threshold may be a fixed value, a relative value, a difference value, an offset value or a percentage value.

At 1104, a receiver detects a received signal and the received signal is filtered. For example, reflections of an interrogation signal transmitted in 1004 of FIG. 10 to measure a fill level of a container are received by a receiver on the sensor device. In some embodiments, the received signal is subject to noise and the received signal is filtered to isolate the desired signal (e.g., band-pass filter the received signal), and amplified (e.g., to improve signal to noise ratio). The received configuration in 806 of FIG. 8 may specify the parameters/configuration of the filter, amplification, automatic gain control, analysis, isolation, etc. In some embodiments, a predetermined beginning portion (e.g., predetermined amount of time in the beginning of the signal) of the received signal may be ignored/removed/muted due to coupling between the transmitter and receiver of the sensor device. For example, when the transmitter transmits the interrogation signal, the signal may be received by the receiver of the sensor device (e.g., conducted directly from the transmitter to the receiver via the housing of the sensor device) before the signal is reflected by the contents of the container, and this undesired signal portion received in the beginning of the received signal is not to be identified as a reflection. In some embodiments, filtering the received signal includes detecting an envelope of the received signal. For example, using a hardware circuit (e.g., analog) and/or software (e.g., digital) signal envelope detector, an upper envelope of the received signal is obtained for use in subsequent steps.

At 1106, a next signal amplitude value of the received filtered signal is selected for analysis. For example, as the received signal is received and filtered, each signal amplitude value of the received signal is selected to be analyzed in the order of the signal. An example of the next signal amplitude value is a next signal value in a stream of signal values comprising the received filtered signal. In some embodiments, the next signal amplitude value of the received filtered signal is a next signal amplitude value of the determined envelope of the received filtered signal.

At 1108, it is determined whether the selected amplitude value meets the reflection detection threshold. In some embodiments, determining whether the selected amplitude value meets the reflection detection threshold includes determining whether the selected signal amplitude value is equal to or greater than the reflection detection threshold. By identifying when the amplitude of the received signal increases to reach the threshold value, the signal location/time at which a reflection is potentially detected in the received signal is identified. For example, potential reflections are detected by identifying instances in the received signal where the amplitude increases to transition from being below the detection threshold to meeting the threshold.

In some embodiments, determining whether the selected amplitude value meets the reflection detection threshold includes determining a difference between a baseline signal amplitude and the selected amplitude value and determining whether the difference meets the reflection detection threshold (e.g., the set reflection detection threshold is a relative value). For example, rather than directly using the raw magnitude value of the selected signal amplitude, a relative difference between the baseline signal amplitude and the selected amplitude value is utilized to compensate for amplitude increase caused by other signal sources (e.g., the difference better measures signal amplitude increase caused by a reflection). The baseline signal amplitude may be preconfigured, specified in a received configuration, and/or dynamically determined. For example, the baseline signal amplitude is determined by averaging signal amplitude (e.g., frequency low pass filter) of the received signal (e.g., envelope of the received signal) for a window of time (e.g., for set amount of latest signal envelope hysteresis). When comparing this difference with the reflection detection threshold (e.g., threshold selected/determined for comparison with difference values), it is determined that the selected amplitude value meets the reflection detection threshold if the difference is greater than or equal to the reflection detection threshold. Otherwise, it is determined that the reflection detection threshold is not met. In some embodiments, the selected amplitude value can only meet the reflection detection threshold if the selected amplitude value is greater than the previous selected amplitude value (e.g., only detect signal increases to threshold).

In some embodiments, once it has been determined that the selected amplitude value has met the reflection detection threshold, a next selected amplitude value in a next iteration of the process is not eligible to meet the reflection detection threshold until a next selected amplitude in a subsequent process iteration falls below (or meets) a detection reset threshold. This reduces the likelihood of detecting another potential reflection for a period of time after a reflection has been identified/detected. For example, although the detection threshold has been met, the amplitude of the received signal may continue to increase or remain high for the same reflection event. In order to prevent subsequent selected amplitude values of the same reflection event from being detected as a new potential reflection, once the selected amplitude value has been determined to meet the reflection detection threshold in 1108, subsequent iterations of 1108 are not eligible to determine that the selected amplitude value meets the reflection detection threshold until the selected amplitude is detected as fallen below (or having met) the detection reset threshold. Thus, in some embodiments, once it is determined at 1108 that the selected amplitude value meets the reflection detection threshold, subsequent iterations of 1108 determines that the selected amplitude value does not meet the reflection detection threshold (regardless of whether the selected amplitude value is greater or equal to the reflection detection threshold) until the selected amplitude value in a subsequent iteration is detected as being less than (or equal to) the detection reset threshold to enable reflection detection again and the selected amplitude value in another subsequent iteration is detected as being equal to or above the reflection detection threshold to determine that the selected amplitude value meets the reflection detection threshold.

In some embodiments, determining whether the selected amplitude value is below (or equal to) the detection reset threshold includes determining a difference between the baseline signal amplitude and the selected amplitude value and determining whether the difference is below (or equal to) the detection reset threshold (e.g., the detection reset threshold is a relative value). It is determined that the selected amplitude value is below (or equal) to the detection reset threshold if the difference is less than (or equal) to the detection reset threshold.

The detection reset threshold is equal in value to the reflection detection threshold in some embodiments, while in other embodiments detection reset threshold is less in value than the reflection detection threshold. In some embodiments, the detection reset threshold is a value that is set (e.g., dynamically varied) along with the reflection detection threshold in 1102. For example, the detection reset threshold is relative (e.g., a fixed amount less, a percentage less, etc.) to the reflection detection threshold.

If at 1108 it is determined that the reflection detection threshold is met, at 1110, the selected amplitude value is identified as corresponding to a potential reflection. For example, a time value associated with the selected amplitude value (e.g., time value of when the selected amplitude value occurs in the received signal, time duration from signal transmission to when the signal portion corresponding to the selected amplitude value was received, etc.) is stored in a data structure tracking potential reflections. In some embodiments, a distance value corresponding to the potential reflection is stored. In some embodiments, because other factors such as noise and other sources of error may also cause the amplitude of the received signal to rise above the detection threshold, the identified received signal portions that exceed the detection threshold are identified as potential reflections because although they likely correspond to reflections that are detected by a receiver, other sources may have caused the detection.

At 1112, it is determined whether reflection detection should be concluded for the fill level measurement instance. In some embodiments, a specified number of potential reflections is to be detected for each fill level measurement instance and if the number of identified potential reflections reaches the specified number (e.g., ten potential reflections to be detected), it is determined to conclude the reflection detection. In some embodiments, potential reflections are to be detected for a specified amount of the received signal (e.g., time length), and when the specified time length of the received signal has been analyzed, it is determined to conclude the reflection detection. In some embodiments, concluding the detection is stopping detection/receipt of the received signal from the receiver. For example, the receiver is powered down and a signal is not detected until a next fill level measurement is performed.

If at 1112 it is determined that reflection detection should not be concluded, the process returns to 1106. If at 1112 it is determined that reflection detection should be concluded, at 1114, the detected potential reflections are indicated and the process ends.

Figure 12:
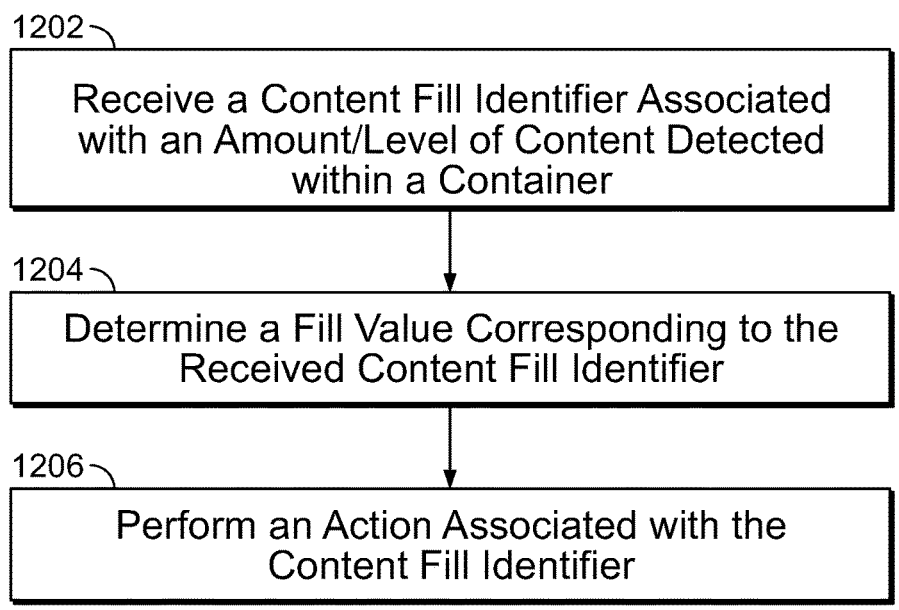
FIG. 12 is a flowchart illustrating an embodiment of a process for performing an action based on a determined content amount.

FIG. 12 is a flowchart illustrating an embodiment of a process for performing an action based on a determined content amount. The process of FIG. 12 may be at least in part implemented on interface device 406 and/or server 410 of FIG. 4.

At 1202, a content fill identifier associated with an amount/level of content detected within a container is received. In some embodiments, the received content fill identifier is the current fill level set in 1012 of FIG. 10. In some embodiments, the content fill identifier has been received along with an associated sensor device identifier of a specific sensor device. The content fill identifier may be utilized to track change in content amount/level of a specific container measured by a sensor device. In some embodiments, the content fill identifier has been received via a local wireless communication protocol (e.g., Wifi, BLUETOOTH Low Energy, etc.). In some embodiments, the content fill identifier is received by interface device 406 of FIG. 4. In some embodiments, the content fill identifier is received by server 410 via network 408 of FIG. 4. In various embodiments, the received content fill identifier is one of a plurality of content fill identifiers received from the same sensor device over time for the same container and/or from different sensor devices for different containers. In some embodiments, the content fill identifier includes a time value associated with the amount of time it took to receive the reflected interrogation signal and/or a distance value associated with the distance traveled by the received reflected interrogation signal.

At 1204, a fill value corresponding to the received content fill identifier is determined. For example, a percentage value and/or a volume amount value corresponding to the received content fill identifier is determined. In some embodiments, using an identifier of a sensor device associated with the received content fill identifier, a container type associated with the received content fill identifier is identified. For example, the identification of a specific container type received in 510 of FIG. 5 has been previously associated with the sensor device identifier and this identification of the container type is retrieved using the sensor device identifier.

In some embodiments, the sensor device identifier and the received content level identifier are provided to server 410 by interface device 406 and server 410 determines the corresponding fill amount/level. In some embodiments, the received content fill identifier identifies the associated container type of the sensor device that transmitted the received content fill identifier.

In some embodiments, a specific container type is associated with a specific table/database/data structure/formula that maps an identifier of the received content fill identifier to an amount/level of content included in a container of the associated container type. For example, the fill percentage and/or volume value that corresponds to the received content fill identifier is determined. In some embodiments, the received content fill identifier is modified before being utilized to obtain the amount/level value using the specific table/database/data structure/formula for the specific container type.

At 1206, an action associated with the content fill identifier is performed. For example, the determined fill value is stored. For example, server 410 of FIG. 4 tracks content remaining within each container being tracked using one or more sensor devices. In some embodiments, performing the action includes performing inventory management. For example, an inventory of a liquor beverage remaining in an opened bottle as well as new bottles stocked on hand are tracked to provide reporting of consumption amount, cost of goods sold, consumption pattern, inventory forecasting, etc.

In some embodiments, performing the action includes providing an alert when it is detected that inventory of the content is low. For example, a mobile application alert on an interface device is provided when the amount/level of content reaches below a threshold value for a single container and/or an inventory across all inventory on hand of the content. In another example, the alert is provided on the sensor device (e.g., flashing light). In some embodiments, the alert is only provided if the amount/level of content reaches below a threshold value. The threshold value may be dynamically determined based on a historical depletion pattern of the content. In some embodiments, an interface device application and/or a webpage is utilized to display and manage inventory of content.

In some embodiments, a database tracks remaining content in each container measured by a sensor device, and for each tracked content stores one or more of the following: sensor device identifier, type of liquid, brand of product, UPC, bar code identifier, quantity remaining, quantity utilized over a time period (e.g., minute/day/week/month/year, etc.), new product container/bottle on hand, price, distributor, date and time of purchase, servings per use, time of servings consumed, location, expiration, chemical composition, odor, color, temperature, humidity, ingredients of the content, and various content composition information (e.g., sulfites, ethyl, etc.). In some embodiments, once sufficient fill values are collected over time, performing the action includes determining a recommended time to reorder, a rate of consumption, an average amount consumed per pour/usage, etc. In some embodiments, a user is able to establish and specify one or more inventory thresholds based on product category, brand, type of beverage, cost, and/or recipes. For example, when the inventory of a product falls below a threshold, a notification may be provided in real-time.

In some embodiments, performing the action includes determining whether the latest determined fill value is larger than a previously determined fill value detected using the same sensor device. For example, it is assumed that containers are not refilled with contents and when contents of a container has been entirely consumed, a user is to replace the empty container with a new full container of the same container type and transfer the sensor device from the empty container to the new full container. The use of a new product container is automatically determined and tracked by detecting whether the latest determined fill value is larger than a previously determined fill value. In some embodiments, if a user desires to utilize a different container type with a sensor device that has been already associated with an existing container type, the user is to reconfigure the sensor device for the new container type.

In some embodiments, performing the action includes obtaining Point of Sale data of items (e.g., mixed drinks, shots, glasses, etc.) sold and correlating the POS data with tracked content inventory depletion. This may offer a view into which types of beverages are in demand, how beverages are consumed, and pairing between different products (e.g., food pairing). Based on this information, a user entity profile may be developed to enable insights into past performance and future forecasting of the user entity's sales metrics. In some embodiments, by analyzing consumption patterns across user entities, geographical regional analysis may be performed to analyze product trends. This information may be utilized to provide recommendations on items to offer for sale based on seasonality, real-time consumption data, and trends for a particular geographical area as well as across a larger region.

In some embodiments, a recipe (e.g., mixed drink recipe) is recommended based on inventory availability of ingredients (e.g., determined amount/level of content), season, consumer profile, holidays, social recommendations, etc. For example, a recipe recommendation service detects the availability of ingredient beverages in real-time, analyzes applicable seasonal/time-based demand profiles of recipes, and suggestions from consumers to recommend the best possible drink recipes to offer. In some embodiments, based on current recipes offered by a user entity and/or new recipes to be offered by the user entity, inventory forecasting is adjusted to provide a recommendation of additional quantities of products/containers to order from one or more distributors. For example, when a new recipe is added, the missing ingredients and/or low inventory ingredients are automatically ordered from the most appropriate distributors (e.g., distributors/merchants selected based on price) in quantities that have been forecasted based on detected product content depletion patterns of the user entity as well as for other user entities (e.g., similar user entities that have already offered the new recipe).

In some embodiments, performing the action includes assisting in ordering additional quantities of the content being tracked. For example, the consumption amount and pattern of the content and amount of full product containers on hand are analyzed to determine how many additional containers of the content should be ordered to replenish the stock inventory of the container. In some embodiments, the order for additional product containers may be automatically provided to a distributor/merchant of the product container to automatically place an order for the content. For example, a user is provided an option to reorder a product from a distributor by allowing the user to automatically send inventory reports periodically to the distributor. In some embodiments, a notification to order additional quantities of a product/content is provided to a user and the user may provide an associated confirmation to automatically place an order for the recommended additional quantities of the product/content from a recommended/preset distributor. Order configuration such as distributor preference, payment information, preferred time of delivery, etc. may be stored and utilized when automatically placing an order.

In some embodiments, a product marketplace with various distributor/merchant options for products is accessible via an interface device such as interface device 406 of FIG. 4. In some embodiments, a device/server is able to locate a distributor's delivery truck or service that is nearby and automatically order/request delivery of one or more products/containers that are preferred to be restocked immediately. For example, when it is detected that additional quantity of a product is required prior to a normal product ordering/delivery schedule, immediate delivery from a nearby source is automatically requested. A user may be provided a notification prior to ordering/delivery to obtain authorization from the user.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A measurement device, comprising:
a transmitter configured to transmit an interrogation signal;
a receiver configured to receive the interrogation signal that has been reflected within a container, wherein the received reflected interrogation signal is used to determine a time value that corresponds to a distance traveled by the interrogation signal and the distance traveled by the interrogation signal corresponds to a fill level of the container; and
a protective barrier covering at least the transmitter or the receiver and at least a portion of the protective barrier is configured to be inserted within the container when the measurement device is engaged with the container, wherein
subject to the protective barrier covering the transmitter, the transmitter transmits the interrogation signal through the protective barrier and the transmitter and the protective barrier are separated by a gap, and
subject to the protective barrier covering the receiver, the receiver receives the interrogation signal through the protective barrier.

2. The device of claim 1, wherein the transmitter is a speaker.

3. The device of claim 1, wherein the interrogation signal includes an ultrasonic signal.

4. The device of claim 1, wherein the receiver is a microphone and at least a portion of the receiver is in contact with a dampening material that is in contact with an assembly of the measurement device.

5. The device of claim 1, wherein the protective barrier is a film.

6. The device of claim 1, wherein the gap is substantially 0.2 mm.

7. The device of claim 1, wherein the protective barrier covers both the transmitter and the receiver.

8. The device of claim 7, wherein the protective barrier is attached to the receiver via an adhesive.

9. The device of claim 1, wherein the transmitter and the receiver are at least in part sealed within the measurement device via a potting material.

10. The device of claim 9, wherein the potting material has been injected into a cavity behind the transmitter.

11. The device of claim 1, wherein the gap includes an air gap.

12. The device of claim 1, further comprising a vent tube.

13. The device of claim 12, wherein the vent tube is at least in part sealed at one end.

14. The device of claim 12, wherein the vent tube includes an opening on a side wall of the vent tube.

15. The device of claim 1, further comprising a drip collector that slopes away from the protective barrier.

16. The device of claim 1, further comprising a battery holder assembly configured to hold at least one battery within a neck of the measurement device configured to be inside the container when the content fill level sensor is engaged with the container.

17. The device of claim 1, further comprising a spout configured to dispense contents of the container while the measurement device is engaged with the container.

18. The device of claim 1, further comprising a sensor holder assembly configured to hold and position the transmitter and the sensor holder assembly is configured to be attached to a battery holder assembly.

19. The device of claim 1, wherein the fill level is provided by the measurement device to a remote device via a wireless signal.

20. A method, comprising:

transmitting an interrogation signal using a transmitter, wherein the transmitter transmits the interrogation signal through a protective barrier covering at least the transmitter or a receiver and subject to the protective barrier covering the transmitter, the transmitter and the protective barrier are separated by a gap, and at least a portion of the protective barrier is configured to be inserted within a container when a measurement device is engaged with the container; and receiving the interrogation signal that has been reflected within the container, wherein the received reflected interrogation signal is used to determine a time value that corresponds to a distance traveled by the interrogation signal and the distance traveled by the interrogation signal corresponds to a fill level of the container.

\* \* \* \* \*